United States Patent
Isoda et al.

(10) Patent No.: US 10,502,743 B2
(45) Date of Patent: Dec. 10, 2019

(54) METHOD FOR DETECTING LUNG SQUAMOUS CELL CARCINOMA

(71) Applicants: Konica Minolta, Inc., Chiyoda-ku, Tokyo (JP); FORERUNNER PHARMA RESEARCH CO., LTD., Meguro-ku, Tokyo (JP)

(72) Inventors: Takeshi Isoda, Sayama (JP); Nao Noro, Fuchu (JP); Tomonori Kaneko, Hachioji (JP)

(73) Assignees: KONICA MINOLTA, INC., Tokyo (JP); CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/434,259

(22) PCT Filed: Oct. 9, 2012

(86) PCT No.: PCT/JP2012/076082
§ 371 (c)(1),
(2) Date: Apr. 8, 2015

(87) PCT Pub. No.: WO2014/057528
PCT Pub. Date: Apr. 17, 2014

(65) Prior Publication Data
US 2015/0276749 A1  Oct. 1, 2015

(51) Int. Cl.
G01N 33/574 (2006.01)
C07K 16/28 (2006.01)
C07K 14/705 (2006.01)

(52) U.S. Cl.
CPC ..... G01N 33/57492 (2013.01); C07K 14/705 (2013.01); C07K 16/28 (2013.01); G01N 33/57423 (2013.01); G01N 2333/705 (2013.01)

(58) Field of Classification Search
CPC ................. G01N 33/57492; G01N 33/57423
See application file for complete search history.

(56) References Cited

U.S. PATENT DOCUMENTS

| | | | |
|---|---|---|---|
| 5,874,531 A | 2/1999 | Strominger et al. | |
| 7,255,861 B1 | 8/2007 | Strominger et al. | |
| 2004/0136997 A1 | 7/2004 | Arlen et al. | |
| 2008/0089900 A1 | 4/2008 | Strominger et al. | |
| 2010/0092457 A1 | 4/2010 | Aburatani et al. | |
| 2011/0312511 A1* | 12/2011 | Winquist ......... | G01N 33/57492 506/9 |
| 2012/0040376 A1 | 2/2012 | Ueda et al. | |

FOREIGN PATENT DOCUMENTS

| | | |
|---|---|---|
| EP | 2050466 A1 | 4/2009 |
| JP | 2004529849 A | 9/2004 |
| JP | 2007186508 A | 7/2007 |
| JP | 2012051822 A | 3/2012 |
| WO | 2008020586 A1 | 2/2008 |
| WO | WO2010/144808 A2 * | 12/2010 |

OTHER PUBLICATIONS

Health, Labour and Welfare Statistics Association, Trend of National Health—Journal of Health and Welfare Statistics, 47:52-53, 2000 with English Abstract, 4 pages.
Practical Method for Reading Tumor Markers (Shuyo Maka no Yomikata no Jissai); Lung Cancer. The Japanese Journal of Clinical and Experimental Medicine 78: 35-40, 2001 with English Abstract, 9 pages.
Cemile Dilara Savci-Heijink, The Role of Desmoglein-3 in the Diagnosis of Squamous Cell Carcinoma of the Lung, The American Journal of Pathology, 2009, vol. 174, No. 5, pp. 1629-1637.
International Search Report corresponding to Application No. PCT/JP2012/076082; dated Nov. 6, 2012.
Written Opinion of the International Searching Authority corresponding to Application No. PCT/JP2012/076082; dated Nov. 6, 2012, with English translation.
Extended European Search Report corresponding to Application No. 12886166.3-1402/2908133 PCT/JP2012/076082; dated Mar. 4, 2016.
Huang C H et al: "Using Desmoglein 1 and 3 Enzyme-linked Immunosorbent Assay as an Adiunct Diagnostic Tool for Pemphigus", Journal of the Chinese Medical Association, Elsevier (Singapore) Pte Ltd, Hong Kong Branch, HK, vol. 70, No. 2, Feb. 1, 2007, pp. 65-70.

* cited by examiner

Primary Examiner — Jessica H Roark
(74) Attorney, Agent, or Firm — Cantor Colburn LLP

(57) ABSTRACT

The present invention provides a method by which lung squamous cell carcinoma can be detected in a simple and prompt manner with high detection performance; and the like. The method according to the present invention detects lung squamous cell carcinoma by an assessment including the steps of: (1) performing measurement of the desmoglein 3 content in a blood sample collected from a subject; and (2) comparing the desmoglein 3 content determined by the measurement with the desmoglein 3 content in a blood sample collected from a healthy individual so as to estimate the presence of lung squamous cell carcinoma in the subject when the desmoglein 3 content is higher in the blood sample collected from the subject.

3 Claims, 4 Drawing Sheets
Specification includes a Sequence Listing.

[Fig. 1]
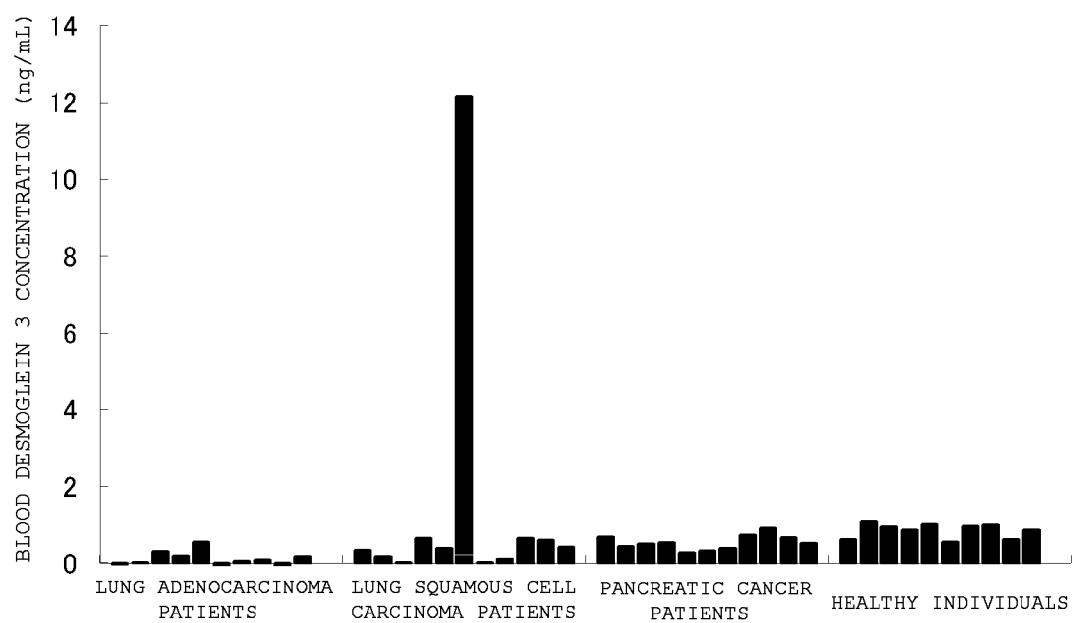

[Fig. 2]
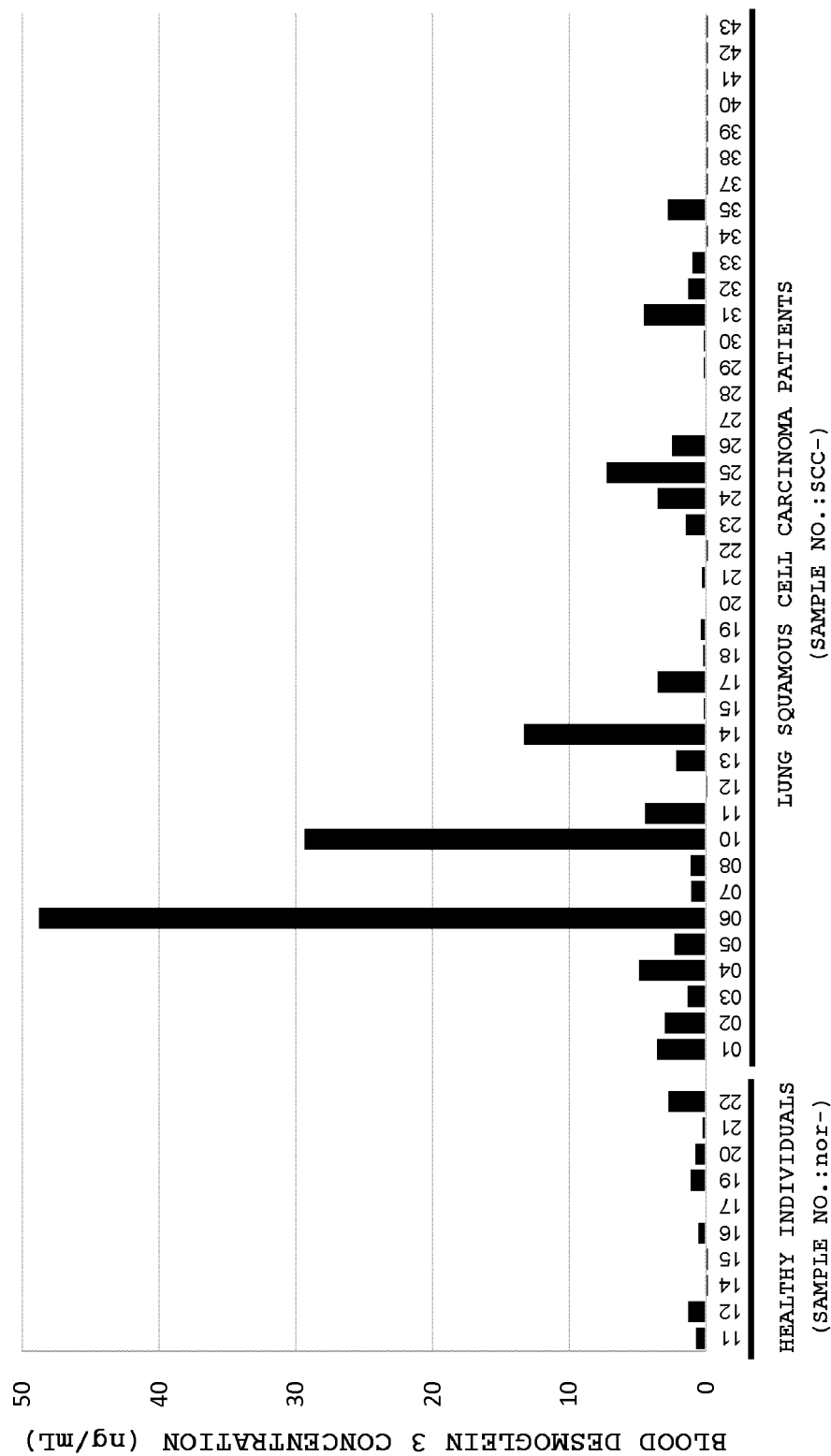

[Fig. 3]
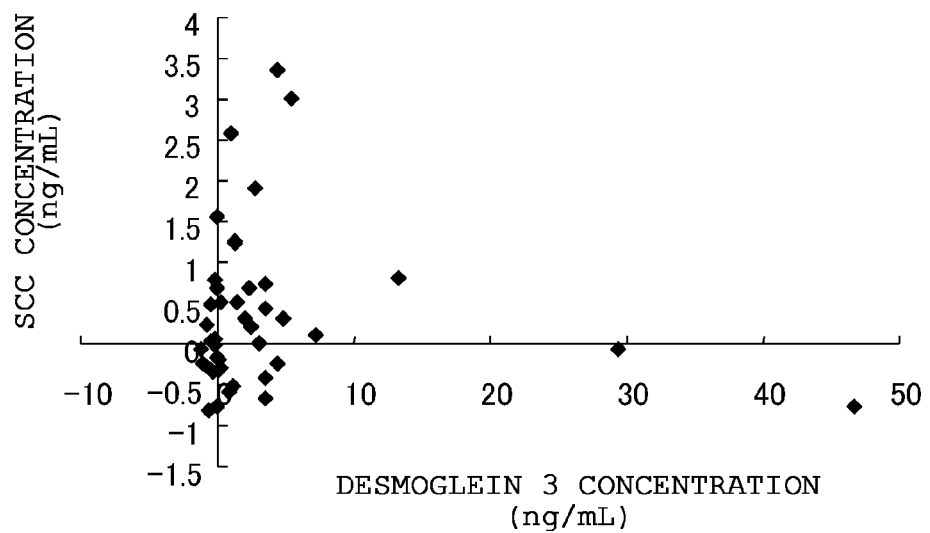
[Fig. 4]
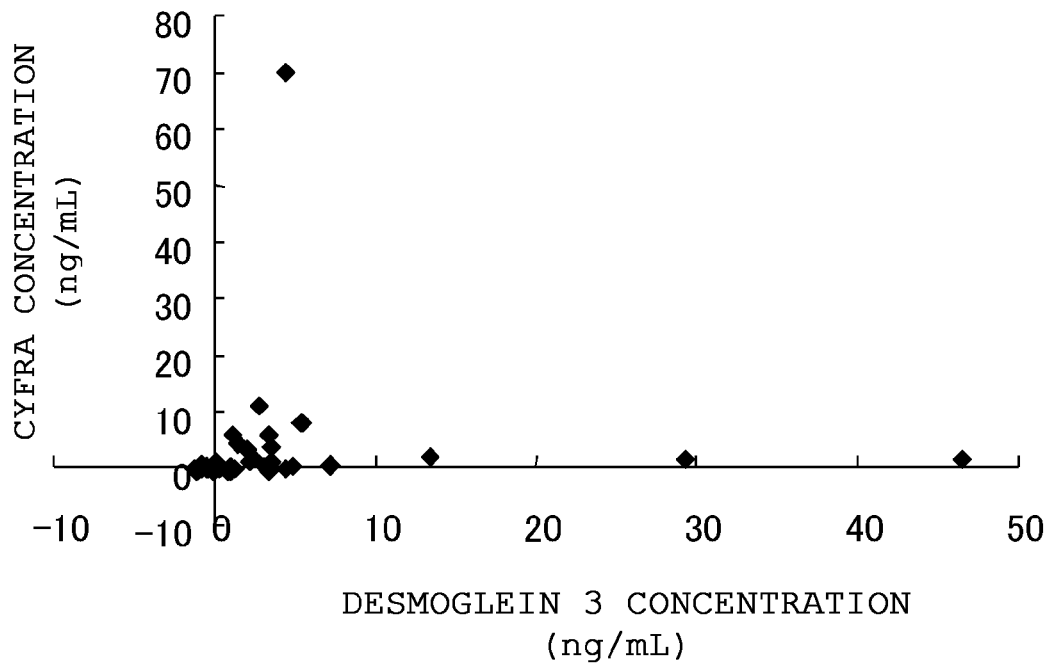

[Fig. 5]
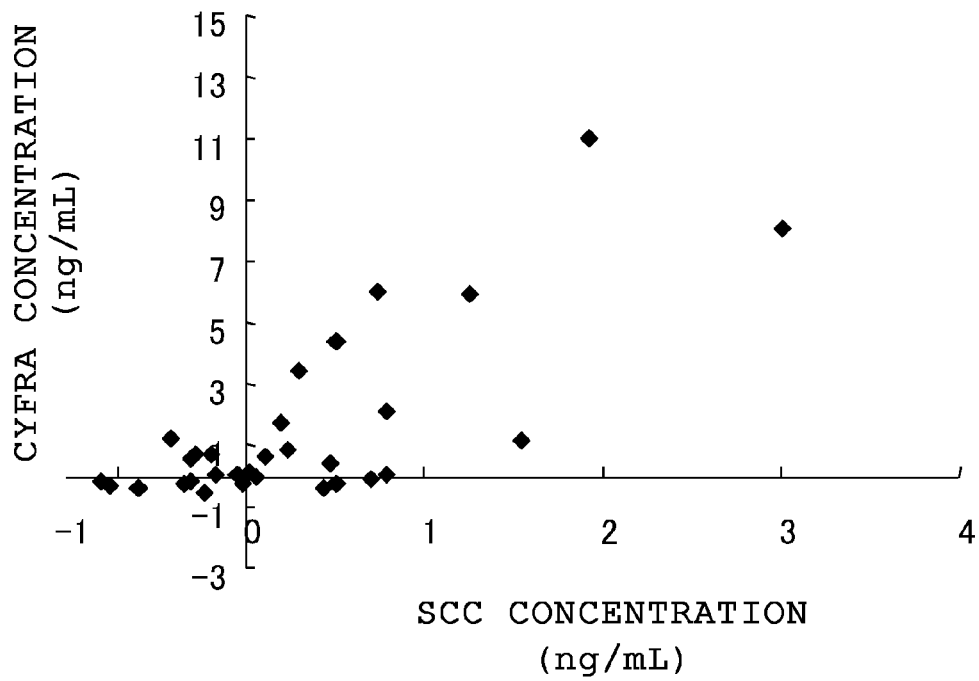
[Fig. 6]
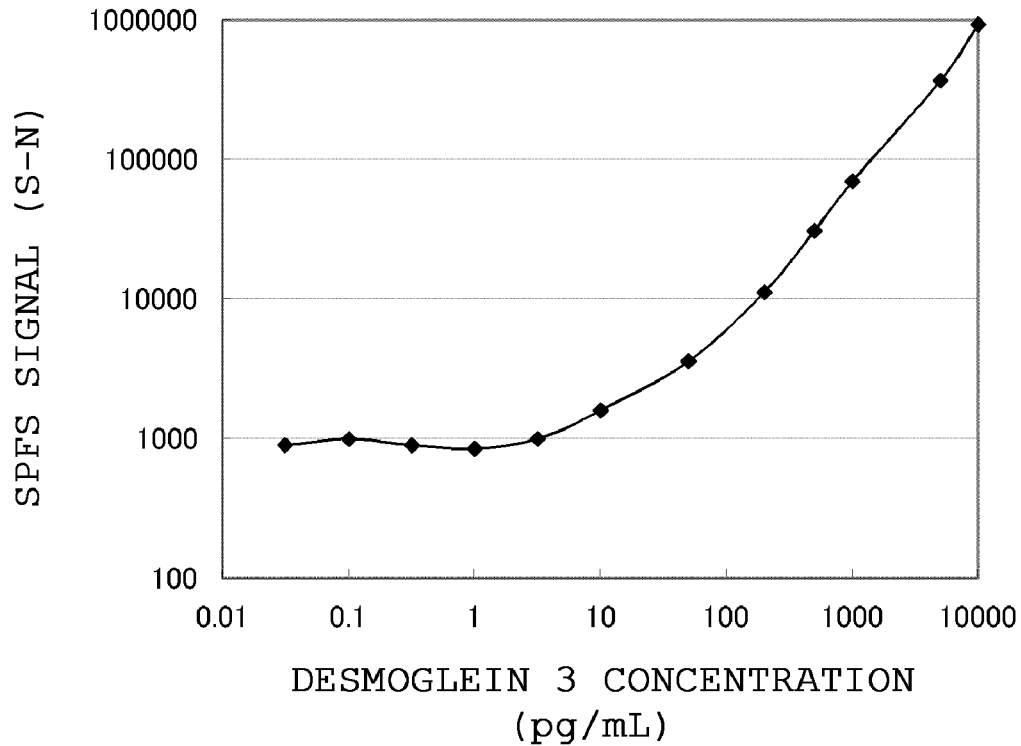

```
                    SEQUENCE LISTING

<160> NUMBER OF SEQ ID NOS: 25

<210> SEQ ID NO 1
<211> LENGTH: 999
<212> TYPE: PRT
<213> ORGANISM: Homo sapiens

<400> SEQUENCE: 1

Met Met Gly Leu Phe Pro Arg Thr Thr Gly Ala Leu Ala Ile Phe Val
1               5                   10                  15

Val Val Ile Leu Val His Gly Glu Leu Arg Ile Glu Thr Lys Gly Gln
                20                  25                  30

Tyr Asp Glu Glu Glu Met Thr Met Gln Gln Ala Lys Arg Arg Gln Lys
            35                  40                  45

Arg Glu Trp Val Lys Phe Ala Lys Pro Cys Arg Glu Gly Glu Asp Asn
        50                  55                  60

Ser Lys Arg Asn Pro Ile Ala Lys Ile Thr Ser Asp Tyr Gln Ala Thr
65                  70                  75                  80

Gln Lys Ile Thr Tyr Arg Ile Ser Gly Val Gly Ile Asp Gln Pro Pro
                85                  90                  95

Phe Gly Ile Phe Val Val Asp Lys Asn Thr Gly Asp Ile Asn Ile Thr
                100                 105                 110

Ala Ile Val Asp Arg Glu Glu Thr Pro Ser Phe Leu Ile Thr Cys Arg
            115                 120                 125

Ala Leu Asn Ala Gln Gly Leu Asp Val Glu Lys Pro Leu Ile Leu Thr
```

```
            130                 135                 140
Val Lys Ile Leu Asp Ile Asn Asp Asn Pro Val Phe Ser Gln Gln
145                 150                 155                 160

Ile Phe Met Gly Glu Ile Glu Asn Ser Ala Ser Asn Ser Leu Val
                165                 170                 175

Met Ile Leu Asn Ala Thr Asp Ala Asp Glu Pro Asn His Leu Asn Ser
                180                 185                 190

Lys Ile Ala Phe Lys Ile Val Ser Gln Glu Pro Ala Gly Thr Pro Met
                195                 200                 205

Phe Leu Leu Ser Arg Asn Thr Gly Glu Val Arg Thr Leu Thr Asn Ser
            210                 215                 220

Leu Asp Arg Glu Gln Ala Ser Ser Tyr Arg Leu Val Val Ser Gly Ala
225                 230                 235                 240

Asp Lys Asp Gly Glu Gly Leu Ser Thr Gln Cys Glu Cys Asn Ile Lys
                245                 250                 255

Val Lys Asp Val Asn Asp Asn Phe Pro Met Phe Arg Asp Ser Gln Tyr
                260                 265                 270

Ser Ala Arg Ile Glu Glu Asn Ile Leu Ser Ser Glu Leu Leu Arg Phe
                275                 280                 285

Gln Val Thr Asp Leu Asp Glu Glu Tyr Thr Asp Asn Trp Leu Ala Val
            290                 295                 300

Tyr Phe Phe Thr Ser Gly Asn Glu Gly Asn Trp Phe Glu Ile Gln Thr
305                 310                 315                 320

Asp Pro Arg Thr Asn Glu Gly Ile Leu Lys Val Val Lys Ala Leu Asp
                325                 330                 335

Tyr Glu Gln Leu Gln Ser Val Lys Leu Ser Ile Ala Val Lys Asn Lys
                340                 345                 350

Ala Glu Phe His Gln Ser Val Ile Ser Arg Tyr Arg Val Gln Ser Thr
                355                 360                 365

Pro Val Thr Ile Gln Val Ile Asn Val Arg Glu Gly Ile Ala Phe Arg
            370                 375                 380

Pro Ala Ser Lys Thr Phe Thr Val Gln Lys Gly Ile Ser Ser Lys Lys
385                 390                 395                 400

Leu Val Asp Tyr Ile Leu Gly Thr Tyr Gln Ala Ile Asp Glu Asp Thr
                405                 410                 415

Asn Lys Ala Ala Ser Asn Val Lys Tyr Val Met Gly Arg Asn Asp Gly
                420                 425                 430

Gly Tyr Leu Met Ile Asp Ser Lys Thr Ala Glu Ile Lys Phe Val Lys
            435                 440                 445

Asn Met Asn Arg Asp Ser Thr Phe Ile Val Asn Lys Thr Ile Thr Ala
450                 455                 460

Glu Val Leu Ala Ile Asp Glu Tyr Thr Gly Lys Thr Ser Thr Gly Thr
465                 470                 475                 480

Val Tyr Val Arg Val Pro Asp Phe Asn Asp Asn Cys Pro Thr Ala Val
                485                 490                 495

Leu Glu Lys Asp Ala Val Cys Ser Ser Ser Pro Ser Val Val Val Ser
                500                 505                 510

Ala Arg Thr Leu Asn Asn Arg Tyr Thr Gly Pro Tyr Thr Phe Ala Leu
                515                 520                 525

Glu Asp Gln Pro Val Lys Leu Pro Ala Val Trp Ser Ile Thr Thr Leu
            530                 535                 540

Asn Ala Thr Ser Ala Leu Leu Arg Ala Gln Glu Gln Ile Pro Pro Gly
545                 550                 555                 560
```

```
Val Tyr His Ile Ser Leu Val Leu Thr Asp Ser Gln Asn Asn Arg Cys
            565                 570                 575
Glu Met Pro Arg Ser Leu Thr Leu Glu Val Cys Gln Cys Asp Asn Arg
            580                 585                 590
Gly Ile Cys Gly Thr Ser Tyr Pro Thr Thr Ser Pro Gly Thr Arg Tyr
            595                 600                 605
Gly Arg Pro His Ser Gly Arg Leu Gly Pro Ala Ala Ile Gly Leu Leu
        610                 615                 620
Leu Leu Gly Leu Leu Leu Leu Leu Ala Pro Leu Leu Leu Leu Thr
625                 630                 635                 640
Cys Asp Cys Gly Ala Gly Ser Thr Gly Val Thr Gly Gly Phe Ile
                645                 650                 655
Pro Val Pro Asp Gly Ser Glu Gly Thr Ile His Gln Trp Gly Ile Glu
            660                 665                 670
Gly Ala His Pro Glu Asp Lys Glu Ile Thr Asn Ile Cys Val Pro Pro
        675                 680                 685
Val Thr Ala Asn Gly Ala Asp Phe Met Glu Ser Ser Glu Val Cys Thr
        690                 695                 700
Asn Thr Tyr Ala Arg Gly Thr Ala Val Glu Gly Thr Ser Gly Met Glu
705                 710                 715                 720
Met Thr Thr Lys Leu Gly Ala Ala Thr Glu Ser Gly Ala Ala Gly
                725                 730                 735
Phe Ala Thr Gly Thr Val Ser Gly Ala Ala Ser Gly Phe Gly Ala Ala
                740                 745                 750
Thr Gly Val Gly Ile Cys Ser Ser Gly Gln Ser Gly Thr Met Arg Thr
                755                 760                 765
Arg His Ser Thr Gly Gly Thr Asn Lys Asp Tyr Ala Asp Gly Ala Ile
        770                 775                 780
Ser Met Asn Phe Leu Asp Ser Tyr Phe Ser Gln Lys Ala Phe Ala Cys
785                 790                 795                 800
Ala Glu Glu Asp Asp Gly Gln Glu Ala Asn Asp Cys Leu Leu Ile Tyr
                805                 810                 815
Asp Asn Glu Gly Ala Asp Ala Thr Gly Ser Pro Val Gly Ser Val Gly
            820                 825                 830
Cys Cys Ser Phe Ile Ala Asp Asp Leu Asp Asp Ser Phe Leu Asp Ser
        835                 840                 845
Leu Gly Pro Lys Phe Lys Lys Leu Ala Glu Ile Ser Leu Gly Val Asp
850                 855                 860
Gly Glu Gly Lys Glu Val Gln Pro Pro Ser Lys Asp Ser Gly Tyr Gly
865                 870                 875                 880
Ile Glu Ser Cys Gly His Pro Ile Glu Val Gln Gln Thr Gly Phe Val
                885                 890                 895
Lys Cys Gln Thr Leu Ser Gly Ser Gln Gly Ala Ser Ala Leu Ser Ala
            900                 905                 910
Ser Gly Ser Val Gln Pro Ala Val Ser Ile Pro Asp Pro Leu Gln His
        915                 920                 925
Gly Asn Tyr Leu Val Thr Glu Thr Tyr Ser Ala Ser Gly Ser Leu Val
        930                 935                 940
Gln Pro Ser Thr Ala Gly Phe Asp Pro Leu Leu Thr Gln Asn Val Ile
945                 950                 955                 960
Val Thr Glu Arg Val Ile Cys Pro Ile Ser Ser Val Pro Gly Asn Leu
                965                 970                 975
```

```
Ala Gly Pro Thr Gln Leu Arg Gly Ser His Thr Met Leu Cys Thr Glu
            980                 985                 990

Asp Pro Cys Ser Arg Leu Ile
        995

<210> SEQ ID NO 2
<211> LENGTH: 453
<212> TYPE: PRT
<213> ORGANISM: Artificial Sequence
<220> FEATURE:
<223> OTHER INFORMATION: DF366 VH - Murine IgG2a CH

<400> SEQUENCE: 2

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ser His Gly Glu Ser Leu Glu Trp Ile
        35                  40                  45

Gly Tyr Ile Tyr Pro Asn Asn Gly Gly Ser Gly Tyr Asn Gln Lys Phe
    50                  55                  60

Lys Ser Lys Ala Thr Leu Thr Val Asp Lys Ser Ser Ser Thr Ala Tyr
65                  70                  75                  80

Met Glu Leu His Ser Leu Thr Ser Glu Asp Ser Ala Val Tyr Tyr Cys
                85                  90                  95

Ala Arg Arg Asp Ser Tyr Tyr Gly Phe Asp Met Ala Trp Phe Ala Tyr
            100                 105                 110

Trp Gly Gln Gly Thr Leu Val Thr Val Ser Ala Ala Lys Thr Thr Ala
        115                 120                 125

Pro Ser Val Tyr Pro Leu Ala Pro Val Cys Gly Asp Thr Thr Gly Ser
    130                 135                 140

Ser Val Thr Leu Gly Cys Leu Val Lys Gly Tyr Phe Pro Glu Pro Val
145                 150                 155                 160

Thr Leu Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Thr Ser Ser Thr Trp Pro Ser Gln Ser Ile Thr Cys Asn Val Ala
        195                 200                 205

His Pro Ala Ser Ser Thr Lys Val Asp Lys Lys Ile Glu Pro Arg Gly
    210                 215                 220

Pro Thr Ile Lys Pro Cys Pro Pro Cys Lys Cys Pro Ala Pro Asn Leu
225                 230                 235                 240

Leu Gly Gly Pro Ser Val Phe Ile Phe Pro Pro Lys Ile Lys Asp Val
                245                 250                 255

Leu Met Ile Ser Leu Ser Pro Ile Val Thr Cys Val Val Val Asp Val
            260                 265                 270

Ser Glu Asp Asp Pro Asp Val Gln Ile Ser Trp Phe Val Asn Asn Val
        275                 280                 285

Glu Val His Thr Ala Gln Thr Gln Thr His Arg Glu Asp Tyr Asn Ser
    290                 295                 300

Thr Leu Arg Val Val Ser Ala Leu Pro Ile Gln His Gln Asp Trp Met
305                 310                 315                 320

Ser Gly Lys Glu Phe Lys Cys Lys Val Asn Asn Lys Asp Leu Pro Ala
                325                 330                 335
```

Pro Ile Glu Arg Thr Ile Ser Lys Pro Lys Gly Ser Val Arg Ala Pro
              340                 345                 350

Gln Val Tyr Val Leu Pro Pro Pro Glu Glu Met Thr Lys Lys Gln
        355                 360                 365

Val Thr Leu Thr Cys Met Val Thr Asp Phe Met Pro Glu Asp Ile Tyr
370                 375                 380

Val Glu Trp Thr Asn Asn Gly Lys Thr Glu Leu Asn Tyr Lys Asn Thr
385                 390                 395                 400

Glu Pro Val Leu Asp Ser Asp Gly Ser Tyr Phe Met Tyr Ser Lys Leu
                405                 410                 415

Arg Val Glu Lys Lys Asn Trp Val Glu Arg Asn Ser Tyr Ser Cys Ser
                420                 425                 430

Val Val His Glu Gly Leu His Asn His His Thr Thr Lys Ser Phe Ser
                435                 440                 445

Arg Thr Pro Gly Lys
        450

<210> SEQ ID NO 3
<211> LENGTH: 214
<212> TYPE: PRT
<213> ORGANISM: Artificial Sequence
<220> FEATURE:
<223> OTHER INFORMATION: DF366 VL - Murine IgG2a CL(kappa)

<400> SEQUENCE: 3

Asp Ile Gln Met Thr Gln Ser Pro Ala Ser Leu Ser Ala Ser Val Gly
1               5                   10                  15

Glu Thr Val Thr Ile Thr Cys Arg Pro Ser Glu Asn Ile Tyr Asn Asn
                20                  25                  30

Leu Ala Trp Tyr Gln Gln Lys Gln Gly Lys Ser Pro Gln Leu Leu Val
            35                  40                  45

Tyr Val Ala Thr Asn Leu Ala Glu Gly Val Pro Ser Arg Phe Ser Gly
        50                  55                  60

Ser Gly Ser Gly Thr Arg Phe Ser Leu Lys Ile Asn Ser Leu Gln Pro
65                  70                  75                  80

Glu Asp Phe Gly Lys Tyr Tyr Cys Gln His Ser Tyr Gly Thr Pro Trp
                85                  90                  95

Thr Phe Gly Gly Gly Thr Lys Leu Glu Ile Lys Arg Ala Asp Ala Ala
                100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
            195                 200                 205

Phe Asn Arg Asn Glu Cys
        210

<210> SEQ ID NO 4
<211> LENGTH: 5

-continued

<210> SEQ ID NO 4
<211> LENGTH: 5
<212> TYPE: PRT
<213> ORGANISM: Mus musculus

<400> SEQUENCE: 4

Asp Tyr Asn Met Asp
1               5

<210> SEQ ID NO 5
<211> LENGTH: 17
<212> TYPE: PRT
<213> ORGANISM: Mus musculus

<400> SEQUENCE: 5

Tyr Ile Tyr Pro Asn Asn Gly Gly Ser Gly Tyr Asn Gln Lys Phe Lys
1               5                   10                  15
Ser

<210> SEQ ID NO 6
<211> LENGTH: 14
<212> TYPE: PRT
<213> ORGANISM: Mus musculus

<400> SEQUENCE: 6

Arg Asp Ser Tyr Tyr Gly Phe Asp Met Ala Trp Phe Ala Tyr
1               5                   10

<210> SEQ ID NO 7
<211> LENGTH: 11
<212> TYPE: PRT
<213> ORGANISM: Mus musculus

<400> SEQUENCE: 7

Arg Pro Ser Glu Asn Ile Tyr Asn Asn Leu Ala
1               5                   10

<210> SEQ ID NO 8
<211> LENGTH: 7
<212> TYPE: PRT
<213> ORGANISM: Mus musculus

<400> SEQUENCE: 8

Val Ala Thr Asn Leu Ala Glu
1               5

<210> SEQ ID NO 9
<211> LENGTH: 9
<212> TYPE: PRT
<213> ORGANISM: Mus musculus

<400> SEQUENCE: 9

Gln His Ser Tyr Gly Thr Pro Trp Thr
1               5

<210> SEQ ID NO 10
<211> LENGTH: 123
<212> TYPE: PRT
<213> ORGANISM: Mus musculus

<400> SEQUENCE: 10

Glu Val Gln Leu Gln Gln Ser Gly Pro Glu Leu Val Lys Pro Gly Ala
1               5                   10                  15
Ser Val Lys Ile Ser Cys Lys Ala Ser Gly Tyr Thr Phe Thr Asp Tyr
            20                  25                  30

Asn Met Asp Trp Val Lys Gln Ser His Gly Glu Ser Leu Glu Trp Ile
            35                  40                  45

Gly Tyr Ile Tyr Pro Asn Asn Gly Gly Ser Gly Tyr Asn Gln Lys Phe
 50                  55                  60

Lys Ser Lys Ala Thr Leu Thr Val Asp Lys Ser Ser Ser Thr Ala Tyr
65                  70                  75                  80

Met Glu Leu His Ser Leu Thr Ser Glu Asp Ser Ala Val Tyr Tyr Cys
                85                  90                  95

Ala Arg Arg Asp Ser Tyr Tyr Gly Phe Asp Met Ala Trp Phe Ala Tyr
            100                 105                 110

Trp Gly Gln Gly Thr Leu Val Thr Val Ser Ala
            115                 120

<210> SEQ ID NO 11
<211> LENGTH: 107
<212> TYPE: PRT
<213> ORGANISM: Mus musculus

<400> SEQUENCE: 11

Asp Ile Gln Met Thr Gln Ser Pro Ala Ser Leu Ser Ala Ser Val Gly
 1               5                  10                  15

Glu Thr Val Thr Ile Thr Cys Arg Pro Ser Glu Asn Ile Tyr Asn Asn
            20                  25                  30

Leu Ala Trp Tyr Gln Gln Lys Gln Gly Lys Ser Pro Gln Leu Leu Val
        35                  40                  45

Tyr Val Ala Thr Asn Leu Ala Glu Gly Val Pro Ser Arg Phe Ser Gly
 50                  55                  60

Ser Gly Ser Gly Thr Arg Phe Ser Leu Lys Ile Asn Ser Leu Gln Pro
65                  70                  75                  80

Glu Asp Phe Gly Lys Tyr Tyr Cys Gln His Ser Tyr Gly Thr Pro Trp
                85                  90                  95

Thr Phe Gly Gly Gly Thr Lys Leu Glu Ile Lys
            100                 105

<210> SEQ ID NO 12
<211> LENGTH: 105
<212> TYPE: PRT
<213> ORGANISM: Mus musculus

<400> SEQUENCE: 12

Ala Lys Thr Thr Ala Pro Ser Val Tyr Pro Leu Ala Pro Val Cys Gly
 1               5                  10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
 50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys
            100                 105

<210> SEQ ID NO 13
<211> LENGTH: 107

```
<212> TYPE: PRT
<213> ORGANISM: Mus musculus

<400> SEQUENCE: 13

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 14
<211> LENGTH: 447
<212> TYPE: PRT
<213> ORGANISM: Mus musculus

<400> SEQUENCE: 14

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ser His Gly Glu Ser Leu Glu Trp Ile
        35                  40                  45

Gly Tyr Ile Tyr Pro Asn Asn Gly Gly Ser Gly Tyr Asn Gln Lys Phe
    50                  55                  60

Lys Ser Lys Ala Thr Leu Thr Val Asp Lys Ser Ser Ser Thr Ala Tyr
65                  70                  75                  80

Met Glu Leu His Ser Leu Thr Ser Glu Asp Ser Ala Val Tyr Tyr Cys
                85                  90                  95

Ala Arg Arg Asp Ser Tyr Tyr Gly Phe Asp Met Ala Trp Phe Ala Tyr
            100                 105                 110

Trp Gly Gln Gly Thr Leu Val Thr Val Ser Ala Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Gln Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Cys Lys Pro Cys Ile Cys Thr Val Pro Glu Val Ser Ser Val
225                 230                 235                 240
```

Phe Ile Phe Pro Pro Lys Pro Lys Asp Val Leu Thr Ile Thr Leu Thr
            245                 250                 255

Pro Lys Val Thr Cys Val Val Asp Ile Ser Lys Asp Asp Pro Glu
            260                 265                 270

Val Gln Phe Ser Trp Phe Val Asp Asp Val Glu Val His Thr Ala Gln
            275                 280                 285

Thr Lys Pro Arg Glu Glu Gln Phe Asn Ser Thr Phe Arg Ser Val Ser
            290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
            355                 360                 365

Ile Thr Asp Phe Phe Pro Glu Asp Ile Thr Val Glu Trp Gln Trp Asn
            370                 375                 380

Gly Gln Pro Ala Glu Asn Tyr Lys Asn Thr Gln Pro Ile Met Asp Thr
385                 390                 395                 400

Asp Gly Ser Tyr Phe Val Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
            435                 440                 445

<210> SEQ ID NO 15
<211> LENGTH: 449
<212> TYPE: PRT
<213> ORGANISM: Mus musculus

<400> SEQUENCE: 15

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ala Tyr
            20                  25                  30

Tyr Met His Trp Val Lys Gln Ser Pro Glu Lys Cys Leu Glu Trp Ile
        35                  40                  45

Gly Gln Ile Asn Pro Ser Thr Gly Gly Thr Thr Tyr Asn Gln Lys Phe
    50                  55                  60

Lys Ala Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Trp Gly Asp Ser Trp Gly Gln Gly Thr Thr Leu Thr Val Ser
            100                 105                 110

Ser Ala Lys Thr Thr Pro Pro Ser Val Tyr Pro Leu Ala Pro Gly Cys
            115                 120                 125

Gly Asp Thr Thr Gly Ser Ser Val Thr Leu Gly Cys Leu Val Lys Gly
        130                 135                 140

Tyr Phe Pro Glu Ser Val Thr Val Thr Trp Asn Ser Gly Ser Leu Ser
145                 150                 155                 160

Ser Ser Val His Thr Phe Pro Ala Leu Leu Gln Ser Gly Leu Tyr Thr
                165                 170                 175

Met Ser Ser Ser Val Thr Val Pro Ser Ser Thr Trp Pro Ser Gln Thr
            180                 185                 190

Val Thr Cys Ser Val Ala His Pro Ala Ser Ser Thr Thr Val Asp Lys
            195                 200                 205

Lys Leu Glu Pro Ser Gly Pro Ile Ser Thr Ile Asn Pro Cys Pro Pro
        210                 215                 220

Cys Lys Glu Cys His Lys Cys Pro Ala Pro Asn Leu Glu Gly Gly Pro
225                 230                 235                 240

Ser Val Phe Ile Phe Pro Pro Asn Ile Lys Asp Val Leu Met Ile Ser
                245                 250                 255

Leu Thr Pro Lys Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Ile Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ser Pro Ile Glu Arg
                325                 330                 335

Thr Ile Ser Lys Ile Lys Gly Leu Val Arg Ala Pro Gln Val Tyr Ile
            340                 345                 350

Leu Pro Pro Pro Ala Glu Gln Leu Ser Arg Lys Asp Val Ser Leu Thr
        355                 360                 365

Cys Leu Val Val Gly Phe Asn Pro Gly Asp Ile Ser Val Glu Trp Thr
    370                 375                 380

Ser Asn Gly His Thr Glu Glu Asn Tyr Lys Asp Thr Ala Pro Val Leu
385                 390                 395                 400

Asp Ser Asp Gly Ser Tyr Phe Ile Tyr Ser Lys Leu Asp Ile Lys Thr
                405                 410                 415

Ser Lys Trp Glu Lys Thr Asp Ser Phe Ser Cys Asn Val Arg His Glu
            420                 425                 430

Gly Leu Lys Asn Tyr Tyr Leu Lys Lys Thr Ile Ser Arg Ser Pro Gly
        435                 440                 445

Lys

<210> SEQ ID NO 16
<211> LENGTH: 218
<212> TYPE: PRT
<213> ORGANISM: Mus musculus

<400> SEQUENCE: 16

Asp Ile Val Leu Thr Gln Ser Pro Ala Ser Leu Ala Val Ser Leu Gly
1               5                   10                  15

Gln Ser Val Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Gly Ala Ser Asp Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

-continued

```
Lys Val Pro Tyr Thr Phe Gly Ser Gly Thr Lys Leu Glu Ile Lys Arg
            100                 105                 110
Ala Asp Ala Ala Pro Thr Val Ser Ile Phe Pro Pro Ser Ser Glu Gln
            115                 120                 125
Leu Thr Ser Gly Gly Ala Ser Val Val Cys Phe Leu Asn Asn Phe Tyr
    130                 135                 140
Pro Lys Asp Ile Asn Val Lys Trp Lys Ile Asp Gly Ser Glu Arg Gln
145                 150                 155                 160
Asn Gly Val Leu Asn Ser Trp Thr Asp Gln Asp Ser Lys Asp Ser Thr
                165                 170                 175
Tyr Ser Met Ser Ser Thr Leu Thr Leu Thr Lys Asp Glu Tyr Glu Arg
            180                 185                 190
His Asn Ser Tyr Thr Cys Glu Ala Thr His Lys Thr Ser Thr Ser Pro
        195                 200                 205
Ile Val Lys Ser Phe Asn Arg Asn Glu Cys
    210                 215
```

<210> SEQ ID NO 17
<211> LENGTH: 5
<212> TYPE: PRT
<213> ORGANISM: Mus musculus

<400> SEQUENCE: 17

```
Ala Tyr Tyr Met His
1               5
```

<210> SEQ ID NO 18
<211> LENGTH: 17
<212> TYPE: PRT
<213> ORGANISM: Mus musculus

<400> SEQUENCE: 18

```
Gln Ile Asn Pro Ser Thr Gly Gly Thr Thr Tyr Asn Gln Lys Phe Lys
1               5                   10                  15
Ala
```

<210> SEQ ID NO 19
<211> LENGTH: 4
<212> TYPE: PRT
<213> ORGANISM: Mus musculus

<400> SEQUENCE: 19

```
Trp Gly Asp Ser
1
```

<210> SEQ ID NO 20
<211> LENGTH: 15
<212> TYPE: PRT
<213> ORGANISM: Mus musculus

<400> SEQUENCE: 20

```
Arg Ala Ser Glu Ser Val Glu Tyr Tyr Gly Thr Ser Leu Met Gln
1               5                   10                  15
```

<210> SEQ ID NO 21
<211> LENGTH: 7
<212> TYPE: PRT
<213> ORGANISM: Mus musculus

<400> SEQUENCE: 21

```
Gly Ala Ser Asp Val Glu Ser
1               5

<210> SEQ ID NO 22
<211> LENGTH: 9
<212> TYPE: PRT
<213> ORGANISM: Mus musculus

<400> SEQUENCE: 22

Gln Gln Ser Arg Lys Val Pro Tyr Thr
1               5

<210> SEQ ID NO 23
<211> LENGTH: 113
<212> TYPE: PRT
<213> ORGANISM: Mus musculus

<400> SEQUENCE: 23

Glu Val Gln Leu Gln Gln Ser Gly Pro Glu Leu Val Lys Pro Gly Ala
1               5                  10                  15

Ser Val Lys Ile Ser Cys Lys Ala Ser Gly Tyr Ser Phe Thr Ala Tyr
            20                  25                  30

Tyr Met His Trp Val Lys Gln Ser Pro Glu Lys Cys Leu Glu Trp Ile
        35                  40                  45

Gly Gln Ile Asn Pro Ser Thr Gly Gly Thr Thr Tyr Asn Gln Lys Phe
    50                  55                  60

Lys Ala Lys Ala Thr Leu Thr Val Asp Lys Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Trp Gly Asp Ser Trp Gly Gln Gly Thr Thr Leu Thr Val Ser
            100                 105                 110

Ser

<210> SEQ ID NO 24
<211> LENGTH: 111
<212> TYPE: PRT
<213> ORGANISM: Mus musculus

<400> SEQUENCE: 24

Asp Ile Val Leu Thr Gln Ser Pro Ala Ser Leu Ala Val Ser Leu Gly
1               5                  10                  15

Gln Ser Val Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Gly Ala Ser Asp Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Tyr Thr Phe Gly Ser Gly Thr Lys Leu Glu Ile Lys
            100                 105                 110

<210> SEQ ID NO 25
<211> LENGTH: 110
<212> TYPE: PRT
<213> ORGANISM: Mus musculus
```

```
<400> SEQUENCE: 25

Ala Lys Thr Thr Pro Pro Ser Val Tyr Pro Leu Ala Pro Gly Cys Gly
1               5                   10                  15

Asp Thr Thr Gly Ser Ser Val Thr Leu Gly Cys Leu Val Lys Gly Tyr
            20                  25                  30

Phe Pro Glu Ser Val Thr Val Thr Trp Asn Ser Gly Ser Leu Ser Ser
        35                  40                  45

Ser Val His Thr Phe Pro Ala Leu Leu Gln Ser Gly Leu Tyr Thr Met
    50              55                  60

Ser Ser Ser Val Thr Val Pro Ser Ser Thr Trp Pro Ser Gln Thr Val
65              70                  75                  80

Thr Cys Ser Val Ala His Pro Ala Ser Ser Thr Thr Val Asp Lys Lys
                85                  90                  95

Leu Glu Pro Ser Gly Pro Ile Ser Thr Ile Asn Pro Cys Pro
            100                 105                 110
```

METHOD FOR DETECTING LUNG SQUAMOUS CELL CARCINOMA

CROSS REFERENCE TO RELATED APPLICATIONS

This is the U.S. national stage of application No. PCT/JP2012/076082, filed on Oct. 9, 2012, the disclosure of which is also incorporated herein by reference.

TECHNICAL FIELD

The present invention relates to a method of detecting lung squamous cell carcinoma. More particularly, the present invention relates to a method of detecting lung squamous cell carcinoma by measuring desmoglein 3 in a blood sample.

BACKGROUND ART

Among various types of cancers, lung cancer has the highest mortality rate in both men and women. The mortality rate of lung cancer in Japan has increased since 1950 and, as a result, the number of lung cancer deaths reached 50,871 in 1998, accounting for about 18% of all malignant tumor deaths. Since 1993, for men, the number of lung cancer deaths has surpassed that of stomach cancer deaths and has been ranked first among malignant tumors (see Non-patent Document 1). Furthermore, on the global scale, approximately 3,000,000 people are dying of lung cancer annually. Once diagnosed with tumor, systemic prognosis is poor, with the 5-year survival rate being mere 13%. However, an early detection and treatment of lung cancer can markedly improve the 5-year survival rate. If the disease is detected early and surgical resection is feasible, the 5-year survival rate increases to 40% (see Patent Document 1).

The basic histological types of lung cancer consist of adenocarcinoma, squamous cell carcinoma, adenosquamous carcinoma, large cell carcinoma and small cell carcinoma. Since the first four types are not largely different in terms of prognosis and therapeutic strategy, they are collectively referred to as non-small cell lung cancer.

The number of non-small cell lung cancer cases accounts for 80 to 85% of the number of all lung cancer cases. Non-small cell lung cancer is characterized by, for example, slow progression as compared to small cell carcinoma and insufficient response to chemotherapy and radiation therapy. Thus, during the stage when the tumor is localized, surgical resection is the first option; however, its treatment outcome is very poor as compared to other carcinomas such as stomach cancer at the same disease stage in the TNM classification. Although attempts have been actively made recently to improve the treatment outcome by multidisciplinary therapy, an effective therapeutic method that leads to complete remission has not been established yet. Therefore, an early detection is important and there is a demand for a simple and prompt test method with good sensitivity.

One example of a simple and prompt test method is measurement of a specific diagnostic marker in blood.

In order to achieve early detection of lung cancer and to improve the clinical management, serum biomarkers for lung cancer have been developed. Nonetheless, their clinical usefulness is still limited. For instance, the amounts of CEA (carcinoembryonic antigen) and CYFRA21-1 (cytokeratin 19 fragment) are elevated in sera of some of non-small cell carcinoma patients. Thus, CEA and CYFRA21-1 are clinically effective for monitoring the disease condition and evaluating the response to a treatment; however, they are not suitable for use in clinical diagnosis. This is because they are known to be associated with smoking and other diseases such as pneumonia as well as other types of cancer and they are thus not capable of detecting early-stage lung cancer (see Patent Document 2).

At present, in addition to the above-described markers, SCC (squamous cell carcinoma related antigens), SLX (sialyl Lewis x-i antigen) and the like are selected as blood diagnostic markers of non-small cell lung cancer and used individually or in combination; however, their positive detection rates for early-stage cancer are still low, and it is thus desired to develop a blood diagnostic marker that surely detects non-small cell lung cancer (see Non-patent Document 2). Furthermore, lung squamous cell carcinoma is known to be different from other non-small cell lung cancers in terms of responses to anticancer agents, and it is thus desired to develop a blood diagnostic marker that specifically detects lung squamous cell carcinoma (see Non-patent Document 3).

In squamous cell carcinoma, a large amount of glycoproteins of tumor cells are circulated into the body fluid of the circulatory system, such as serum, or bronchial secretions; therefore, enabling to detect a circulating antigen by ELISA using a monoclonal antibody is a feasible approach to early detection. Detection of tumor markers such as PSA and CEA corresponds to this approach (see Patent Document 1).

Desmoglein 3, which is a member of the cadherin family involved in cell adhesion, is a membrane protein molecule that is particularly highly expressed topically in the lung squamous cell carcinoma tissue, and its usefulness as a diagnostic marker of lung squamous cell carcinoma has been shown (see, for example, Patent Document 3 and Non-patent Document 3).

However, these previous reports all evaluated the expression of desmoglein 3 in cancer tissues by using mRNA or immunohistological staining, so that not only it was required to collect lung cancer tissues from patients by biopsy but also the subsequent analytical work was complicated; therefore, the methods used in these reports cannot be viewed as simple and prompt methods of examining lung squamous cell carcinoma.

Particularly, taking into consideration the properties, functional mechanism and the like of desmoglein 3 molecule, it is speculated that there is hardly any possibility for desmoglein 3 present in cancer tissues and the like to leak into blood. Thus, although there have been reports of studies on the use of a desmoglein 3-containing cadherin family molecule as a tumor marker to be detected by immunohistochemical staining (see Patent Document 3 and Non-patent Document 3), no study has been conducted on the use of desmoglein 3 as a serum marker. That is, the cell adhesion-related cadherin family molecules have a structural characteristic of being embedded in the cell membrane like an anchor and are largely different from other membrane proteins because of this feature.

Furthermore, the presence of an autoantibody for desmoglein 3 has been known, and it is detected even in the blood of a healthy individual. Accordingly, it is easily expected that, even if desmoglein 3 is present in blood, it would be neutralized or inactivated by the autoantibody. When the autoantibody is excessively expressed, it reacts with desmoglein 3 involved in the adhesion of normal skin cells and inhibits the adhesion, and this appears as an autoimmune disease called pemphigus. Even in the blood of healthy individuals and non-pemphigus patients in which the autoantibody is not excessively expressed, the autoantibody is detected in a trace amount.

PRIOR ART REFERENCES

Patent Documents

[Patent Document 1] JP-A-2004-529849
[Patent Document 2] JP-A-2012-51822
[Patent Document 3] WO2008/020586 A1

NON-PATENT DOCUMENTS

[Non-patent Document 1] Health, Labour and Welfare Statistics Association, Trend of National Health—Journal of Health and Welfare Statistics, 47:52-53, 2000
[Non-patent Document 2] Practical Method for Reading Tumor Markers (*Shuyo Maka no Yomikata no Jissai*); Lung Cancer. The Japanese Journal of Clinical and Experimental Medicine 78: 35-40, 2001
[Non-patent Document 3] Savci-Heijink et al., The American Journal of Pathology, vol. 174, No. 5, 1629-1637, 2009

SUMMARY OF THE INVENTION

Problems to be Solved by the Invention

An object of the present invention is to provide a method capable of detecting lung squamous cell carcinoma and prompt manner. Another object of the present invention is to provide a method of detecting lung squamous cell carcinoma with a further improved detection performance. Yet another object of the present invention is to provide a method of detecting blood desmoglein 3 with an improved sensitivity in the detection of lung squamous cell carcinoma.

Technical Solution

In order to solve the above-described problems, the present inventors intensively studied and discovered that desmoglein 3, despite being a cadherin family protein, is present specifically in the blood of lung squamous cell carcinoma patients at a high concentration. The present inventors also discovered that blood desmoglein 3 shows an expression pattern different from those of existing lung cancer markers; that a lung squamous cell carcinoma patient undetectable by an existing lung cancer marker can be detected using blood desmoglein 3; and that the use of blood desmoglein 3 in combination with an existing lung cancer marker further improves the detection performance of lung squamous cell carcinoma. The present inventors further discovered that desmoglein 3 in a blood sample can be detected with high sensitivity by sandwich immunoassay using a combination of specific anti-desmoglein 3 antibodies, thereby completing the present invention. That is, the present invention encompasses the following items.

[1] A method of detecting lung squamous cell carcinoma by an assessment comprising the steps of:
(1) performing measurement of the desmoglein 3 content in a blood sample collected from a subject; and
(2) comparing the desmoglein 3 content determined by the measurement with the desmoglein 3 content in a blood sample collected from a healthy individual so as to estimate the presence of lung squamous cell carcinoma in the subject when the desmoglein 3 content is higher in the blood sample collected from the subject.

[2] The method according to [1], further incorporating an assessment based on the expression level of at least one selected from the group consisting of SCC and CYFRA, which are existing lung cancer markers, obtained from a sample of the same subject.

[3] The method according to [1] or [2], wherein the measurement is performed by sandwich immunoassay.

[4] The method according to [3], wherein the sandwich immunoassay uses: as an immobilized antibody, a DF366m antibody having HCDR1 represented by the amino acid sequence shown in SEQ ID NO:4, HCDR2 represented by the amino acid sequence shown in SEQ ID NO:5, HCDR3 represented by the amino acid sequence shown in SEQ ID NO:6, LCDR1 represented by the amino acid sequence shown in SEQ ID NO:7, LCDR2 represented by the amino acid sequence shown in SEQ ID NO:8 and LCDR3 represented by the amino acid sequence shown in SEQ ID NO:9; and, as a detection antibody, a DF151 antibody having HCDR1 represented by the amino acid sequence shown in SEQ ID NO:17, HCDR2 represented by the amino acid sequence shown in SEQ ID NO:18, HCDR3 represented by the amino acid sequence shown in SEQ ID NO:19, LCDR1 represented by the amino acid sequence shown in SEQ ID NO:20, LCDR2 represented by the amino acid sequence shown in SEQ ID NO:21 and LCDR3 represented by the amino acid sequence shown in SEQ ID NO:22, or an MAB1720 antibody (R&D Systems, Inc.).

[5] The method according to [3] or [4], wherein, in the sandwich immunoassay, the sample is brought into contact with the DF366m antibody immobilized on a carrier and then with the DF151 antibody or the MAB1720 antibody (R&D Systems, Inc.).

[6] The method according to [4] or [5], wherein the DF366m antibody is a complete antibody comprising an H chain represented by the amino acid sequence shown in SEQ ID NO:2 and an L chain represented by SEQ ID NO:3, or an antibody comprising an H chain having the amino acid sequence shown in SEQ ID NO:10 as VH and an L chain having the amino acid sequence shown in SEQ ID NO:11 as VL; and the DF151 antibody is a complete antibody comprising an H chain represented by the amino acid sequence shown in SEQ ID NO:15 and an L chain represented by SEQ ID NO:16, or an antibody comprising an H chain having the amino acid sequence shown in SEQ ID NO:23 as VH and an L chain having the amino acid sequence shown in SEQ ID NO:24 as VL.

[7] The method according to any one of [3] to [6], wherein the sandwich immunoassay is sandwich ELISA.

[8] The method according to any one of [3] to [6], wherein the sandwich immunoassay is SPFS.

[9] A kit for diagnosing lung squamous cell carcinoma, the kit comprising the following reagents used in sandwich immunoassay:
(1) as an immobilized antibody, a DF366m antibody having HCDR1 represented by the amino acid sequence shown in SEQ ID NO:4, HCDR2 represented by the amino acid sequence shown in SEQ ID NO:5, HCDR3 represented by the amino acid sequence shown in SEQ ID NO:6, LCDR1 represented by the amino acid sequence shown in SEQ ID NO:7, LCDR2 represented by the amino acid sequence shown in SEQ ID NO:8 and LCDR3 represented by the amino acid sequence shown in SEQ ID NO:9; and
(2) as a detection antibody, a DF151 antibody having HCDR1 represented by the amino acid sequence shown in SEQ ID NO:17, HCDR2 represented by the amino acid sequence shown in SEQ ID NO:18, HCDR3 represented by the amino acid sequence shown in SEQ ID NO:19, LCDR1 represented by the amino acid sequence shown in SEQ ID NO:20, LCDR2 represented by the amino acid sequence shown in SEQ ID NO:21 and LCDR3 represented by the amino acid sequence shown in SEQ ID NO:22, or an MAB1720 antibody (R&D Systems, Inc.).

[10] The kit for diagnosing lung squamous cell carcinoma according to [9], wherein the DF366m antibody is a complete antibody comprising an H chain represented by the amino acid sequence shown in SEQ ID NO:2 and an L chain represented by SEQ ID NO:3, or an antibody comprising an H chain having the amino acid sequence shown in SEQ ID NO:10 as VH and an L chain having the amino acid sequence shown in SEQ ID NO:11 as VL; and the DF151 antibody is a complete antibody comprising an H chain represented by the amino acid sequence shown in SEQ ID NO:15 and an L chain represented by SEQ ID NO:16, or an antibody comprising an H chain having the amino acid sequence shown in SEQ ID NO:23 as VH and an L chain having the amino acid sequence shown in SEQ ID NO:24 as VL.

[11] The kit for diagnosing lung squamous cell carcinoma according to [9] or [10], further comprising:

(3) a reagent for detecting at least one lung cancer marker selected from the group consisting of SCC and CYFRA using sandwich immunoassay.

Advantageous Effects of Invention

According to the present invention, a simple and prompt method of detecting lung squamous cell carcinoma can be provided. In addition, a lung squamous cell carcinoma patient undetectable by an existing lung cancer marker can be detected, and the detection performance of lung squamous cell carcinoma is further improved by using an existing lung cancer marker in combination. Furthermore, by sandwich immunoassay using a combination of specific antibodies, desmoglein 3 in a blood sample can be detected with high sensitivity in a simple and prompt manner and the detection performance of lung squamous cell carcinoma can be still further improved.

BRIEF DESCRIPTION OF DRAWINGS

FIG. 1 is a graph showing the results of measuring the desmoglein 3 concentration in blood samples collected from healthy individuals, pancreatic cancer patients, lung adenocarcinoma patients and lung squamous cell carcinoma patients (10 subjects each).

FIG. 2 is a graph showing the results of measuring the desmoglein 3 concentration in blood samples collected from lung squamous cell carcinoma patients (40 patients).

FIG. 3 is a graph showing the correlation between the desmoglein 3 concentration and the SCC concentration in the blood samples collected from lung squamous cell carcinoma patients (40 patients).

FIG. 4 is a graph showing the correlation between the desmoglein 3 concentration and the CYFRA21-1 concentration in the blood samples collected from lung squamous cell carcinoma patients (40 patients).

FIG. 5 is a graph showing the correlation between the SCC concentration and the CYFRA21-1 concentration in the blood samples collected from lung squamous cell carcinoma patients (40 patients).

FIG. 6 is a graph showing the results of measuring the amount of desmoglein 3 contained in a buffer by SPFS.

DESCRIPTION OF EMBODIMENTS

The method of detecting lung squamous cell carcinoma according to the present invention will now be described in detail.

The term "sandwich immunoassay" used herein means a method of detecting the presence and amount of an antigen by using two different types of antibodies (immobilized antibody and detection antibody) that recognize different epitopes on the antigen to be detected. Unless otherwise specified, "desmoglein 3" means "human desmoglein 3 protein" shown in SEQ ID NO:1 The term "blood" refers to, for example, whole blood, whole blood that has been subjected to an anticoagulation treatment as required, plasma obtained by centrifuging anticoagulated whole blood and removing the blood cell components, or serum obtained by coagulating whole blood and removing the resulting precipitates (blood clots). The term "blood sample" refers to, in addition to the "blood" described above, a blood-derived sample obtained by subjecting the "blood" to a treatment(s) such as centrifugation, dilution and/or mixing with a reagent as required. The term "subject" refers to a human. Further, the expression "X to Y" representing a numerical range refers to "not less than X and not more than Y".

The present invention includes a method of detecting lung squamous cell carcinoma of a subject by measuring the amount of desmoglein 3 contained in the blood of the subject. The detection method and diagnostic kit of the present invention as well as the anti-desmoglein 3 monoclonal antibodies and sandwich immunoassay of the present invention will now be described in detail.

<Method of Detecting Lung Squamous Cell Carcinoma>

In the present invention, lung squamous cell carcinoma is detected by measuring desmoglein 3 in a blood sample collected from a subject. Since an increase in the blood desmoglein 3 concentration is specific to lung squamous cell carcinoma patients, desmoglein 3 is an effective diagnostic marker of lung squamous cell carcinoma and can be used in the diagnosis of lung squamous cell carcinoma or to support the diagnosis. According to the present invention, lung squamous cell carcinoma can be detected simply by measuring the blood desmoglein 3 concentration; therefore, it is not required to perform tissue biopsy that imposes a large burden on the subject. In addition, since the subsequent analytical work is also easy, lung squamous cell carcinoma can be detected in a simple and prompt manner.

The desmoglein 3 content in a sample can be measured by any method as long as it is capable of specifically detecting desmoglein 3 protein in a blood sample with a required sensitivity; however, it is usually measured by immunoassay because of its high specificity and simplicity. As the immunoassay, from the standpoint of improving the detection sensitivity and specificity, sandwich immunoassay is preferred. As the sandwich immunoassay, sandwich ELISA is preferred from the standpoint of simplicity and SPFS is preferred from the standpoint of detection sensitivity. Further, it is preferred that the antibodies used in the sandwich immunoassay be a combination of the below-described specific antibodies.

Examples of immunoassay other than sandwich immunoassay include a surface plasmon resonance (SPR) method using BIAcore (manufactured by Biacore).

A blood sample to be used can be collected from a subject by a well-known method, and the blood sample is preferably peripheral blood collected from an arm vein of the subject. The collected blood sample may be treated as appropriate by a known method, and it is preferred that serum or plasma be separated therefrom and used.

In the method of detecting lung squamous cell carcinoma, the assessment of the presence of lung squamous cell carcinoma in a subject comprises the steps of:

(1) performing measurement of the desmoglein 3 content in a blood sample collected from a subject; and (2) comparing the desmoglein 3 content determined by the measurement with the desmoglein 3 content in a blood sample collected from a healthy individual so as to estimate the presence of lung squamous cell carcinoma in the subject when the desmoglein 3 content is higher in the blood sample collected from the subject.

The desmoglein 3 content in a blood sample collected from a healthy subject may be measured as a control sample simultaneously in parallel with each measurement; however, it is also possible to measure the desmoglein 3 content in blood samples collected from a certain number of healthy individuals in advance by the same method and use the measured values as known values of healthy individuals against which comparisons are made.

In the comparison of the desmoglein 3 content between a blood sample collected from a subject and a blood sample collected from a healthy individual, when the desmoglein 3 content in the blood sample collected from the subject is higher (the concentration is higher), the presence of lung squamous cell carcinoma in the subject can be estimated. An assessment of "high content" is obtained when the value of the desmoglein 3 concentration in a blood sample is not smaller than an appropriate preset cut-off value. Accordingly, the presence of lung squamous cell carcinoma is estimated (positive assessment) when the desmoglein 3 concentration in a blood sample is not less than a cut-off value, while the absence of lung squamous cell carcinoma is estimated (negative assessment) when the desmoglein 3 concentration in a blood sample is less than a cut-off value.

The cut-off value can be adjusted as appropriate in accordance with the conditions of the detection method, such as the detection limit value, the purpose of the assessment (e.g., screening, definitive diagnosis) and the like. For example, since the desmoglein 3 concentration is 5 ng/mL or less in healthy individuals as shown in FIG. 2, a false-negative assessment can be eliminated by setting the cut-off value at not less than 5 ng/mL. Meanwhile, when the cut-off value is set at less than 5 ng/mL, false-positives in which a healthy individual is assessed as positive occur; however, the ratio of positive assessment for the presence of lung squamous cell carcinoma is increased.

In the assessment of cancer, it is generally desired to determine a suspect patient as positive and proceed to the subsequent diagnosis and treatments without overlooking such a patient; therefore, the cut-off value tends to be set toward increasing the ratio of positive assessments even if false positives are included therein. For example, in Example 4 (FIG. 2), if the cut-off value were set at 5 ng/mL, 4 out of 40 patients would be assessed as positive, with the positive ratio being 10% (false-positive ratio=0%). Meanwhile, if the cut-off value were set at 1 ng/mL, 20 out of 40 patients would be assessed as positive, with the positive ratio being 50% (false-positive ratio=30%).

Taking into consideration the results shown in FIG. 2, in an attempt to devise a more accurate assessment method, it is thought of improving the quantitative accuracy in the low concentration range. Among a total of 50 subjects consisting of 40 lung squamous cell carcinoma patients and 10 healthy individuals, 20 subjects yielded samples that could not be measured due to a content lower than the quantitation limit of 0.2 ng/mL. If the desmoglein 3 concentration in these samples can be measured accurately, it is thought of, for example, setting the cut-off value at 0.2 ng/mL or less, and this potentially enables to institute more preferred assessment criteria.

Alternatively, when a subject is recognized to have a statistically significant difference in terms of desmoglein 3 concentration against blood samples collected from a certain number of healthy individuals, the presence of lung squamous cell carcinoma may be estimated in the subject.

<Method of Detecting Lung Squamous Cell Carcinoma Using Existing Lung Cancer Marker(s) in Combination>

The present invention includes a method of detecting lung squamous cell carcinoma, the method comprising a combination of the above-described assessment based on the desmoglein 3 content in a blood sample collected from a subject and an assessment based on the expression level of an existing lung cancer marker obtained from a sample of the same subject.

The assessment of the desmoglein 3 content in a blood sample collected from a subject is carried out by the method described for the above-described method of detecting lung squamous cell carcinoma.

The existing lung cancer marker may be any lung cancer marker as long as the amount thereof in blood varies significantly between lung cancer patients and healthy individuals, and examples of such an existing lung cancer marker include SCC, CYFRA, CEA and SLX. Thereamong, from the standpoint of improving the detection performance of lung squamous cell carcinoma, it is preferred that the existing lung cancer marker be at least one selected from the group consisting of SCC and CYFRA. These lung cancer markers are highly specific to lung squamous cell carcinoma (Japanese Journal of Cancer and Chemotherapy, 28:2089-2093, 2001) and show an expression tendency different from that of desmoglein 3; therefore, these lung cancer markers can together detect lung squamous cell carcinoma that they cannot detect individually, and it is preferred to use these lung cancer markers in combination because the detection performance is thereby improved.

<Detection of Desmoglein 3 by Sandwich Immunoassay>

In the present invention, it is preferred to measure the desmoglein 3 protein contained in a test sample by sandwich immunoassay using an anti-desmoglein 3 antibody. As the sandwich immunoassay, sandwich ELISA or surface plasmon-field enhanced fluorescence spectroscopy (hereinafter, referred to as "SPFS") is more preferred.

The sandwich immunoassay of the present invention can be performed based on a known method; however, it is preferably performed by the following steps.

(1) Adsorption (Immobilization) of Anti-Desmoglein 3 Antibody (Immobilized Antibody) to Support (Solid Phase)

Examples of a support (carrier) used for immobilization of an anti-desmoglein 3 antibody include insoluble polysaccharides such as agarose and cellulose; synthetic resins such as silicon resins, polystyrene resins, polyacrylamide resins, nylon resins and polycarbonate resins; and insoluble supports such as glass. These supports are used in the form of beads, a plate or the like. In the case of a bead-form support, for example, a column filled therewith can be used. As a plate-form support, for example, a multi-well plate (e.g., a 96-multiwell plate) or a biosensor chip can be used. An anti-desmoglein 3 antibody and such a support can be bound with each other by a commonly used method such as chemical bonding or physical adsorption. As all of these supports, commercially available supports can be suitably employed.

(2) Blocking of Solid Phase

In order to prevent desmoglein 3 in a sample from non-specifically binding to a support, it is preferred to perform blocking of the solid phase. The blocking can be performed using, for example, buffer-diluted bovine serum albumin (BSA), gelatin or albumin. The blocking can be usually performed by incubation at 4° C. to 37° C. for 1 hour to 24 hours or so.

(3) Binding of Desmoglein 3 and Immobilized Antibody

By bringing a test sample into contact with an antibody immobilized on a support, desmoglein 3 and the immobilized antibody are bound with each other. As required, the test sample is appropriately diluted with a buffer, blood, protein-containing solution or the like before being used. As the buffer, for example, a phosphate buffer, a Tris buffer, a citrate buffer, a borate buffer or a carbonate buffer can be used. Further, as the blood, for example, bovine serum can be suitably used and, as the protein-containing solution, a BSA-containing buffer or the like can be suitably used. The contact can be usually made by incubation at 4° C. to 37° C. for 1 hour to 24 hours or so.

In the method of detecting desmoglein 3 according to the present invention, in addition to a test sample for which the desmoglein 3 content is detected, control samples can also be prepared as appropriate. Examples of the control samples include a desmoglein 3-free negative control sample and a desmoglein 3 standard-containing positive control sample. In this case, by comparing the results obtained for the test sample with the results obtained for the desmoglein 3-free negative control sample and the results obtained for the desmoglein 3 standard-containing positive control sample, the presence or absence of desmoglein 3 in the test sample can be verified.

Further, after preparing a series of control samples in which the desmoglein 3 concentration is changed in a stepwise manner and obtaining detection results for each of the control samples in the form of numerical values, the desmoglein 3 contained in the test sample can be quantitatively detected according to a standard curve produced based on the desmoglein 3 concentration values of the control samples and their corresponding measurement values.

(4) Binding of Desmoglein 3 and Detection Antibody

Binding between the desmoglein 3 bound with the immobilized antibody and a detection antibody is performed by bringing the detection antibody into contact with the desmoglein 3. This binding between the desmoglein 3 and the detection antibody is usually performed in a buffer. As the buffer, for example, a phosphate buffer, a Tris buffer, a citrate buffer, a borate buffer or a carbonate buffer can be used. The contact can be usually made by incubation at 4° C. to 37° C. for 1 hour to 24 hours or so.

The detection antibody is obtained by labeling an anti-desmoglein 3 antibody with a labeling substance. The labeling of an anti-desmoglein 3 antibody can be performed by a known method.

As the labeling substance, one which is known to those of ordinary skill in the art, such as a fluorescent dye, an enzyme, a coenzyme, a chemiluminescent substance or a radioactive substance, can be used.

Examples of the fluorescent dye include organic fluorescent dyes such as fluorescent dyes of the fluorescein family (Integrated DNA Technologies, Inc.), fluorescent dyes of the polyhalofluorescein family (Applied Biosystems Japan Ltd.), fluorescent dyes of the hexachlorofluorescein family (Applied Biosystems Japan Ltd.), florescent dyes of the coumarin family (Invitrogen), fluorescent dyes of the rhodamine family (GE Healthcare Bioscience Co., Ltd.), fluorescent dyes of the cyanine family, fluorescent dyes of the indocarbocyanine family, fluorescent dyes of the oxazine family, fluorescent dyes of the thiazine family, fluorescent dyes of the squaraine family, fluorescent dyes of the chelated lanthanide family, fluorescent dyes of the BODIPY (registered trademark) family (Invitrogen), fluorescent dyes of the naphthalenesulfonate family, fluorescent dyes of the pyrene family, fluorescent dyes of the triphenylmethane family, and Alexa Fluor (registered trademark) dye series (Invitrogen).

Further, examples of the fluorescent dye also include rare earth (e.g., Eu and Tb) complex-based fluorescent dyes (e.g., ATBTA-$Eu^{3+}$); fluorescent proteins such as blue fluorescent proteins (BFPs), cyan fluorescent proteins (CFPs), green fluorescent proteins (GFPs), yellow fluorescent proteins (YFPs), red fluorescent proteins (DsReds) and allophycocyanin (APC; LyoFlogen (registered trademark)); and fluorescent fine particles of latex, silica and the like.

In cases where a blood-derived sample is analyzed, in order to minimize the effect of light absorption by iron originating from the blood cell components in blood, it is desired to use a fluorescent dye having a maximum fluorescence wavelength in the near-infrared region, such as Cy5 or Alexa Fluor 647.

Examples of the radioactive substance include radioisotopes (e.g., $^{32}P$, $^{14}C$, $^{125}I$, $^{3}H$ and $^{131}I$).

In cases where biotin is used as a labeling substance, it is preferred that an addition of a biotin-labeled antibody be followed by a further addition of avidin bound with an enzyme such as alkaline phosphatase. For binding of a labeling substance with an anti-desmoglein 3 antibody, a known method such as a glutaraldehyde method, a maleimide method, a pyridyl disulfide method or a periodic acid method can be employed.

Examples of other embodiment of the method of detecting desmoglein 3 according to the present invention include a method which uses at least one primary antibody that specifically recognizes desmoglein 3 protein and at least one secondary antibody that specifically recognizes the primary antibody.

For example, after allowing an anti-desmoglein 3 antibody (primary antibody) of a type different from the antibody bound to the support to bind with desmoglein 3 protein, a secondary antibody capable of binding only to the primary antibody is allowed to react with the resulting complex of desmoglein 3 and the primary antibody. Examples of such a secondary antibody capable of binding only to the primary antibody include, but not limited to, antibodies that specifically bind to a constant region of a class intrinsic to the primary antibody (IgM, IgD, IgG, IgE or IgA) or isotype (IgG1, IgG2, IgG3 or IgG4). Such an anti-desmoglein 3 antibody can be isolated using a known hybridoma technology, or can also be isolated as a recombinant antibody obtained by in-frame ligation of an antibody gene encoding a specific anti-desmoglein 3 antibody with an antibody gene encoding a constant region of a desired class or an isotype. For example, a method which detects desmoglein 3 contained in a test sample by qualitatively or quantitatively detecting the secondary antibody bound as a result of the above-described operation can be employed. In this case, it is appropriate that the secondary antibody be labeled with the above-described labeling substance.

(5) Detection of Labeling Substance

Detection of a labeling substance can be performed by a method that is suitable for each labeling substance and known to those of ordinary skill in the art. For example, a detection antibody labeled with a radioactive substance can be detected by liquid scintillation or an RIA method. A detection antibody labeled with a fluorescent dye can be detected using a luminometer, an SPFS measurement apparatus or the like. In cases where an enzyme-labeled detection antibody is detected, after an addition of a substrate corresponding to the labeling enzyme, the chemical changes of the substrate by the enzyme, such as color development, fluorescence and chemiluminescence, are measured, thereby the detection antibody can be detected.

It is appropriate to perform a washing step for removal of unreacted antibodies, reagents and the like between the above-described steps of (1) to (5). The solvent used for this washing is not particularly restricted as long as it does not adversely affect the steps of the sandwich immunoassay; however, a buffer is usually used. As the buffer, for example, a phosphate buffer, a Tris buffer, a citrate buffer, a borate buffer or a carbonate buffer can be used. In order to improve the washing effect, a surfactant-containing buffer can be used and, for example, a 0.02% polyoxyethylene sorbitan monolaurate (Tween-20, trade name)-containing phosphate buffer (pH 7.4) is preferably used.

[Sandwich ELISA]

Among sandwich immunoassay methods, sandwich ELISA is preferably used in the present invention. Sandwich ELISA is the above-described sandwich immunoassay wherein an enzyme is used as a labeling substance.

As the enzyme, a known enzyme can be used, and examples thereof include luciferase, peroxidase, myeloperoxidase, alkaline phosphatase, β-galactosidase, β-glucosidase, horseradish peroxidase, glucoamylase, lysozyme, saccharide oxidase and microperoxidase.

As an enzyme substrate, a known substrate may be used and, for example, a substrate which develops color as a result of an enzyme reaction (hereinafter, referred to as "color-developing substrate"), a substrate which emits fluorescence (hereinafter, referred to as "fluorescent substrate") or a substrate which emits chemiluminescence (hereinafter, referred to as "chemiluminescent substrate") can be preferably used.

Examples of the color-developing substrate include 3,3'-diaminobenzidine (DAB), 2,2-azinobis(3-ethylbenzothiazoline-6-sulfonic acid)diammonium salt (ABTS), 1,2-phenylenediamine (ortho-phenylenediamine), o-phenylenediamine dihydrochloride (OPD) and 3,3',5,5'-tetramethylbenzidine (TMB).

Examples of the fluorescent substrate include AttoPhos (registered trademark), SPECTROFLUOR (registered trademark), 10-Acetyl-3,7-dihydroxyphenoxazine (ADHP) and QuantaBlu (registered trademark).

Examples of the chemiluminescent substrate include luminol-based compounds (e.g., luminol) and dioxetane-based compounds (e.g., AMPPD (registered trademark), CSPD (registered trademark) and CDP-Star (registered trademark)).

[Sandwich ELISA (Plate ELISA) Using Multiplate]

Examples of a preferred measurement method using sandwich ELISA of the present invention include the following method that uses a multiplate as a carrier (support).

An anti-desmoglein 3 antibody to be immobilized (captured) diluted with a sodium hydrogen carbonate buffer is added to a multi-well plate, which is then incubated overnight at 4° C. to immobilize the antibody on the plate.

Next, after removing the antibody solution and washing the plate with PBS, 1% BSA-PBS(−) (blocking solution) is added and the plate is incubated at room temperature for 2 hours to perform blocking. Subsequently, after removing the blocking solution and washing the plate with PBS, a test sample is added and the plate is incubated at room temperature for 1 hour, thereby allowing desmoglein 3 to bind with the immobilized antibody.

After the incubation, the test sample is removed and the plate is washed with PBS. Then, a labeled antibody is added and the plate is incubated at room temperature for 1 hour. Subsequently, after removing the labeled antibody and washing the plate with PBS three times, a substrate solution is added and the resulting enzyme reaction product is measured.

[Surface Plasmon-Field Enhanced Fluorescence Spectroscopy: SPFS)]

As the sandwich immunoassay of the present invention, SPFS can be preferably employed. SPFS is a method which utilizes a phenomenon that, when an excitation light is irradiated to a metal thin film formed on a dielectric member at an angle at which an attenuated total reflection (ATR) occurs, an evanescent wave transmitting through the metal thin film is enhanced by several tens to several hundred times due to resonance with surface plasmon, thereby efficiently exciting a fluorescent material labeling an analyte (a substance to be analyzed) captured in the vicinity of the metal thin film, and measures the fluorescent signal thereof. Such SPFS is extremely highly sensitive as compared to common fluorescent labeling methods and the like; therefore, it is capable of quantifying an analyte even when the analyte exists only in a trace amount in a sample.

<SPFS Measurement Member>

An SPFS measurement member generally has a constitution in which a sensor chip, on which an area for forming a sandwich-type immunocomplex and performing fluorescence measurement by SPFS (assay area) is formed, is laminated with a member for constructing a flow path or well, which is capable of retaining, on the assay area, a variety of solutions (e.g., an analyte-containing sample, a labeled ligand solution and other reaction reagents) that are used for the formation of the sandwich-type immunocomplex and the like.

The sensor chip basically comprises: a transparent support for introducing an excitation light to the back of a metal thin film; a metal thin film for generating surface plasmon resonance, which is formed on the transparent support; and a reaction layer for capturing an analyte on the sensor surface, which is formed on the metal thin film. As required, the sensor chip may further comprise a spacer layer for inhibiting metal quenching of fluorescence caused by excessive proximity of a fluorescent material to the metal thin film, which spacer layer is formed between the metal thin film and the reaction layer.

The part where the reaction layer is formed corresponds to the assay area. The assay area may be arranged by forming the reaction layer on the entire bottom surface of the flow path or well, or by forming the reaction layer only on a part of the bottom surface (with a desired pattern, as required). The size of the assay area can be adjusted, taking into consideration the irradiation area of the excitation light that is usually a laser light. For example, when the spot diameter of the excitation light is about 1 mmφ, the assay area is usually designed in such a manner to have a size of at least several millimeters square.

In the case of a "flow path-type" SPFS system in which various solutions are transferred through a closed flow path, the measurement member is assembled by mounting on the sensor chip a "flow cell" having holes for forming a flow path and, as required, further mounting thereon a "top plate" having a liquid inlet port and a liquid outlet port at the positions corresponding to the holes of the flow cell, in such a manner that the sensor chip and the flow cell (and the top plate) are tightly adhered and fixed with each other. The sensor chip surface at the positions corresponding to the holes of the flow cell constitutes the bottom surface of a flow path, on which an assay area is formed. In such a flow path-type system, for example, using a liquid-transferring means including a pump and a tube, various liquids can be fed to the flow path via the liquid inlet port and discharged via the liquid outlet port and, as required, the liquids can also be transferred in a reciprocating manner or a circulating manner. The conditions such as the liquid transfer rate and the liquid transfer (circulation) time can be adjusted as appropriate, taking into consideration the sample amount, the analyte concentration in the sample, the sizes of the flow path and the well, the mode of the reaction layer (e.g., the immobilized ligand density), the pump performance and the like.

Meanwhile, in the case of a "well-type" SPFS system in which various solutions are retained in a space larger than the above-described flow path, the measurement member is assembled by mounting and fixing, on the sensor chip, a "well member" having a through-hole(s) for forming a well(s). In such a well-type system, various liquids can be added to the well(s) and removed therefrom using a pipet-form member or the like.

The flow cell can be made of, for example, a sheet-form polydimethylsiloxane (PDMS). The top plate is prepared from a transparent material so that the fluorescence emitted from the assay area can be measured, and the top plate can be made of, for example, a plate-form polymethyl methacrylate (PMMA). Alternatively, the flow cell and the top plate can be made of a plastic that is molded or photolithographed into a desired shape.

The means for tightly adhering and fixing the flow cell or well member on the sensor chip is not particularly restricted, and these processes can be generally performed by physical application of pressure from the top and the bottom. If necessary, an adhesive, a matching oil, a transparent adhesive sheet or the like that has the same light refractive index as that of the transparent support may also be used.

<SPFS Measurement Apparatus>

The immunoassay according to the present invention can be performed using a common SPFS measurement apparatus. Basically, an SPFS measurement apparatus has a detachable SPFS measurement member and comprises: a light source for irradiating an excitation light (preferably a laser light) having a wavelength appropriate for the fluorescent material to be used; a prism for allowing the excitation light to enter the back surface of a metal thin film formed on a sensor chip at a prescribed angle (when a planar substrate-form sensor chip is used as a transparent support); a light receiver which receives light reflected by the metal thin film and measures its intensity; a lens for condensing fluorescent light emitted from the fluorescent material; a detector for measuring the intensity of the fluorescent light; various filters for allowing only a portion of the excitation light and fluorescent light that has a prescribed wavelength to transmit therethrough and cutting other light; and the like. For a more concrete mode, reference can be made to various documents such as JP-A-2010-145272.

<SPFS Measurement Method>

The SPFS measurement method according to the present invention measures desmoglein 3 contained in a blood sample as a target and comprises the following steps 1 and 2:

(Step 1) the step of forming a sandwich-type immunocomplex containing an immobilized anti-desmoglein 3 antibody, desmoglein 3 and a fluorescently labeled anti-desmoglein 3 antibody; and (Step 2) the step of measuring the intensity of fluorescence emitted from a fluorescent material contained in the thus formed sandwich-type immunocomplex by SPFS (surface plasmon-field enhanced fluorescence spectroscopy).

The mode of the step of forming a sandwich-type immunocomplex indicated as the step 1 is not particularly restricted as long as a sandwich-type immunocomplex can be formed before proceeding to the step 2; however, the step 1 generally takes, for example, a mode which comprises the following steps 1a and 1b:

(Step 1 a) the step of forming a complex by allowing the above-described immobilized anti-desmoglein 3 antibody to react with desmoglein 3 contained in a sample; and (Step 1b) the step of forming the above-described sandwich-type immunocomplex by allowing the thus formed immunocomplex to react with the above-described fluorescently labeled anti-desmoglein 3 antibody.

It is noted here that, as required, a washing step for washing the flow path or well with a washing liquid (e.g., a surfactant solution) may also be incorporated between the step 1a and the step 1b or between the step 1 (step 1b) and the step 2.

Meanwhile, the step 2 can take the same mode as in common SPFS in that an excitation light is irradiated to a metal thin film to generate an evanescent wave enhanced by surface plasmon resonance occurring on the metal thin film and the intensity of fluorescence (corresponding to "signal") emitted from the fluorescent material (of a fluorescently labeled ligand) contained in the sandwich-type immunocomplex is thereby measured. Further, before the step 2 or in a region outside the assay area, it is preferred to irradiate an excitation light to the metal thin film in the same manner as in the step 2 without a sandwich-type immunocomplex being formed thereon, measure the intensity of the generated fluorescence (corresponding to "noise") and then correct the above-described signal value with the thus obtained noise value (by subtraction or division).

When measuring the intensity of the fluorescence emitted from the fluorescent material in the step 2, the flow path and the well are usually kept in a state of being filled with an aqueous solvent (e.g., a phosphate buffer) that does not contain any analyte or fluorescently labeled antibody; however, the flow path and the well can also be in a state of being filled with a solvent other than such an aqueous solvent or with air.

The concentration of desmoglein 3 contained in the analyzed sample can be quantified based on the signal value determined in the above-described manner (which is preferably corrected with the noise) and a calibration curve separately prepared using samples with known concentrations.

The desmoglein 3 concentration in a sample that is determined in this manner can be used as reference data when diagnosing various diseases or symptoms for which the desmoglein 3 functions as a biomarker.

<Anti-Desmoglein 3 Monoclonal Antibody>

[Antibody Used in Immunoassay]

In the immunoassay according to the present invention, an anti-human desmoglein 3 antibody is used. The anti-human desmoglein 3 antibody to be used in the measurement of the present invention is not particularly restricted as long as it can achieve the effects of the present invention, and examples thereof include antibodies obtained by the method described in Patent Document 3, specifically DF120, DF122, DF148, DF151, DF153, DF168, DF331, DF364, DF366, DF151c, DF364c, DF366c, DF366m and YB-DF366c. The amino acid sequences of some of these anti-human desmoglein 3 antibodies are disclosed in Patent Document 3. Further, commercially available anti-human desmoglein 3 antibodies other than those described above can be also used. Examples of suitable commercially available antibodies include MAB1720 manufactured by R&D Systems, Inc. and D219-3 manufactured by Medical & Biological Laboratories Co., Ltd.

[Immobilized Antibody and Detection Antibody]

In the sandwich immunoassay according to the present invention, an immobilized antibody (hereinafter, also referred to as "capturing antibody") and a detection antibody are used. The immobilized antibody is immobilized on a support (carrier) and specifically captures desmoglein 3 contained in a sample. The detection antibody is an antibody modified with a substance used for detection (hereinafter, referred to as "labeling substance") and binds to the desmoglein 3 captured by the immobilized antibody, thereby labeling the desmoglein 3 with the labeling substance. By measuring the presence and the amount of this labeling substance, the presence and the amount of desmoglein 3 in the sample can be determined. In the present invention, by using the below-described specific anti-human desmoglein 3 antibodies as an immobilized antibody and a detection antibody, blood desmoglein 3 can be detected with an improved sensitivity.

[Combination of Antibodies to be Used]

In the sandwich immunoassay according to the present invention, it is preferred to use two antibodies selected from the group consisting of the below-described DF366m antibody, DF151 antibody and MAB1720 antibody.

As a combination of antibodies to be used in the sandwich immunoassay of the present invention, it is more preferred to use the DF366m antibody as an immobilized antibody and the DF151 antibody or the MAB1720 antibody as a detection antibody. From the standpoint of improving the detection sensitivity, it is still more preferred to use the DF366m antibody as an immobilized antibody and the DF151 antibody as a detection antibody.

<DF366m Antibody>

The DF366m antibody is a monoclonal antibody having: HCDR1 represented by the amino acid sequence shown in SEQ ID NO:4; HCDR2 represented by the amino acid sequence shown in SEQ ID NO:5; HCDR3 represented by the amino acid sequence shown in SEQ ID NO:6; LCDR1 represented by the amino acid sequence shown in SEQ ID NO:7; LCDR2 represented by the amino acid sequence shown in SEQ ID NO:8; and LCDR3 represented by the amino acid sequence shown in SEQ ID NO:9, and the DF366m antibody encompasses a complete antibody comprising an H chain represented by the amino acid sequence shown in SEQ ID NO:2 and an L chain represented by SEQ ID NO:3 (hereinafter, referred to as "DF366m[I] antibody") as well as an antibody comprising a portion of the amino acids of the complete antibody (hereinafter, referred to as "DF366m[P] antibody"). It is noted here that the above-described CDRs of the DF366m antibody are each the same as the corresponding CDRs of the DF366 antibody (see Patent Document 3).

<DF366m[P] Antibody>

The DF366m[P] antibody is an antibody comprising a portion of the amino acids of the DF366m[I] antibody, and encompasses the following group of antibodies.

(1) An antibody in which at least all of the CDR regions are identical to those of the DF366m[I] antibody (hereinafter, referred to as "DF366m[CDR] antibody"), that is, an antibody comprising:

an H chain having the amino acid sequence shown in SEQ ID NO:4 (HCDR1 sequence of the DF366m antibody) as CDR1, the amino acid sequence shown in SEQ ID NO:5 (HCDR2 sequence of the DF366m antibody) as CDR2 and the amino acid sequence shown in SEQ ID NO:6 (HCDR3 sequence of the DF366m antibody) as CDR3; and an L chain having the amino acid sequence shown in SEQ ID NO:7 (LCDR1 sequence of the DF366m antibody) as CDR1, the amino acid sequence shown in SEQ ID NO:8 (LCDR2 sequence of the DF366m antibody) as CDR2 and the amino acid sequence shown in SEQ ID NO:9 (LCDR3 sequence of the DF366m antibody) as CDR3.

(2) An antibody in which at least the variable regions (V regions) are identical to those of the DF366m[I] antibody (hereinafter, referred to as "DF366m[V] antibody"), that is, an antibody comprising: an H chain having the amino acid sequence shown in SEQ ID NO:10 (VH sequence of the DF366m antibody) as VH; and an L chain having the amino acid sequence shown in SEQ ID NO:11 (VL sequence of the DF366m antibody) as VL.

(3) An antibody in which at least the Fab region is identical to that of the DF366m[I] antibody (hereinafter, referred to as "DF366m[Fab]"), that is, an antibody comprising: the V regions described in the above (2); an H chain having the amino acid sequence shown in SEQ ID NO:12 (CH1 sequence of the DF366m antibody) as CH1; and an L chain having the amino acid sequence shown in SEQ ID NO:13 (CL sequence of the DF366m antibody) as CL.

One preferred example of the DF366m[V] antibody is an antibody comprising an H chain having the amino acid sequence shown in SEQ ID NO:14 (a chimeric antibody of VH having the amino acid sequence shown in SEQ ID NO:10 and CH of mouse IgG1) and an L chain having the amino acid sequence shown in SEQ ID NO:3 (which antibody corresponds to the (naturally occurring-type) DF366 described in Patent Document 3).

From the standpoint of improving the detection sensitivity, the antibody used in the present invention is preferably the DF366m[V] antibody, the DF366m[Fab] antibody or the DF366m[I] antibody, more preferably the DF366m[Fab] antibody or the DF366m[I] antibody, still more preferably the DF366m[I] antibody.

<DF151 Antibody>

The DF151 antibody is a monoclonal antibody having: HCDR1 represented by the amino acid sequence shown in SEQ ID NO:17; HCDR2 represented by the amino acid sequence shown in SEQ ID NO:18; HCDR3 represented by the amino acid sequence shown in SEQ ID NO:19; LCDR1 represented by the amino acid sequence shown in SEQ ID NO:20; LCDR2 represented by the amino acid sequence shown in SEQ ID NO:21; and LCDR3 represented by the amino acid sequence shown in SEQ ID NO:22, and the DF151 antibody encompasses a complete antibody comprising an H chain represented by the amino acid sequence shown in SEQ ID NO:15 and an L chain represented by SEQ ID NO:16 (hereinafter, referred to as "DF151[I] antibody") as well as an antibody comprising a portion of the amino acids of the complete antibody (hereinafter, referred to as "DF151 [P] antibody").

<DF151[P] Antibody>

The DF151[P] antibody is an antibody comprising a portion of the amino acids of the DF151[I] antibody, and encompasses the following group of antibodies.

An antibody in which at least all of the CDR regions are identical to those of the DF151[I] antibody (hereinafter, referred to as "DF151[CDR] antibody"), that is, an antibody comprising:

an H chain having the amino acid sequence shown in SEQ ID NO:17 (HCDR1 sequence of the DF151 antibody) as CDR1, the amino acid sequence shown in SEQ ID NO:18 (HCDR2 sequence of the DF151 antibody) as CDR2 and the amino acid sequence shown in SEQ ID NO:19 (HCDR3 sequence of the DF151 antibody) as CDR3; and an L chain having the amino acid sequence shown in SEQ ID NO:20 (LCDR1 sequence of the DF151 antibody) as CDR1, the amino acid sequence shown in SEQ ID NO:21 (LCDR2 sequence of the DF151 antibody) as CDR2 and the amino acid sequence shown in SEQ ID NO:22 (LCDR3 sequence of the DF151 antibody) as CDR3.

(2) An antibody in which at least the variable regions (V regions) are identical to those of the DF151[I] antibody (hereinafter, referred to as "DF151[V] antibody"), that is, an antibody comprising: an H chain having the amino acid sequence shown in SEQ ID NO:23 (VH sequence of the DF151 antibody) as VH; and an L chain having the amino acid sequence shown in SEQ ID NO:24 (VL sequence of the DF151 antibody) as VL.

(3) An antibody in which at least the Fab region is identical to that of the DF151[I] antibody (hereinafter, referred to as "DF151[Fab] antibody"), that is, an antibody comprising: the V regions described in the above (2); an H chain having the amino acid sequence shown in SEQ ID NO:25 (CH1 sequence of the DF151 antibody) as CH1; and an L chain having the amino acid sequence shown in SEQ ID NO:3 (CL sequence of the DF151 antibody) as CL.

From the standpoint of improving the detection sensitivity, the antibody used in the present invention is preferably the DF151[V] antibody, the DF151[Fab] antibody or the DF151[I] antibody, more preferably the DF151[Fab] antibody or the DF151[I] antibody, still more preferably the DF151[I] antibody.

<MAB1720 Antibody>

The MAB1720 antibody is a mouse anti-human desmoglein 3 monoclonal antibody (subclass: IgG$_{2b}$) produced by Clone #216519 and can be purchased from R&D Systems, Inc.

[Low-Molecular-Weight Antibody, Multimer, Chimeric Antibody, etc.]

The antibody used in the present invention is not restricted to a full-length antibody molecule (complete antibody). Within a range where the effects of the present invention are not adversely affected and with a proviso that the antibody has the amino acid sequences of the respective CDRs prescribed above, the antibody used in the present invention may also be a low-molecular-weight antibody, a multimer, a chimeric antibody or a humanized antibody. Examples of the low-molecular-weight antibody include Fab, Fab', F(ab')$_2$, Fv, scFv (single-chain Fv), diabody and sc(Fv)$_2$ (single-chain (Fv)$_2$). Further, multimers of these antibodies (e.g., dimers, trimers, tetramers and polymers) are also included in the antibodies of the present invention. Moreover, a chimeric antibody or a humanized antibody can be prepared by a known method.

From the standpoint of improving the detection sensitivity, the antibody used in the present invention is preferably a complete antibody, F(ab')$_2$ or Fab, more preferably a complete antibody or F(ab')$_2$, still more preferably a complete antibody. In the present invention, since an antibody is used in an immobilized or labeled form, it is appropriate to use an antibody having an amino acid sequence of an adequate length that comprises a region utilized for immobilization onto a sensor chip or binding of a labeling substance (preferably a constant region that is not involved in binding with desmoglein 3). Those of ordinary skill in the art are capable of appropriately selecting such an antibody.

[Substitution, Deletion, Addition and/or Insertion of Amino Acid(s)]

In the amino acid sequence of the antibody used in the present invention, within a range that does not adversely affect the effects of the present invention, an amino acid(s) may be substituted, deleted, added and/or inserted. That is, those antibodies that have the same amino acid sequence as that of the antibody used in the present invention except that one or more amino acids constituting the antibody are mutated, which antibodies are functionally equivalent to the antibody used in the present invention in terms of the effects to be achieved in the present invention, are also included in the antibodies used in the present invention. In such mutants, the number of mutated amino acids is usually 50 amino acids or less, preferably 30 amino acids or less, more preferably 10 amino acids or less (for example, 5 amino acids or less). The above-described amino acid substitution is preferably conservative amino acid substitution.

It is already known that polypeptides having a modified amino acid sequence, in which one or more amino acid residues of a certain amino acid sequence are deleted, added and/or substituted with other amino acids, retain their original biological activities (Mark, D. F. et al., Proc. Natl. Acad. Sci. USA (1984) 81:5662-5666; Zoller, M. J. and Smith, M., Nucleic Acids Research (1982) 10:6487-6500; Wang, A. et al., Science 224:1431-1433; and Dalbadie-McFarland, G. et al., Proc. Natl. Acad. Sci. USA (1982) 79:6409-6413). However, it is desired to avoid substitution, deletion, addition and/or insertion of an amino acid in the amino acid sequences of the above-described CDRs.

[Method of Preparing Antibody]

The above-described antibodies used in the present invention can each be prepared by a known method. A desired antibody can be obtained by, for example, introducing a nucleic acid having a sequence that encodes the amino acids of the desired antibody into an expression plasmid, introducing this expression plasmid into appropriate expression cells and then culturing the expression cells in an appropriate culture medium (see, for example, Patent Document 3).

<Sample>

The sample to be analyzed by the method of the present invention is a blood sample collected from a subject. The blood may be, for example, whole blood, whole blood that has been subjected to an anticoagulation treatment as required, plasma obtained by centrifuging anticoagulated whole blood and removing the blood cell components, or serum obtained by coagulating whole blood and removing the resulting precipitates (blood clots). Further, the blood sample also includes, in addition to the above-described blood, blood-derived samples obtained by subjecting the above-described blood to a treatment(s) such as centrifugation, dilution and/or mixing with a reagent as required. Thereamong, the blood sample is preferably serum or plasma.

<Kit for Diagnosing Lung Squamous Cell Carcinoma>

The present invention includes a kit for diagnosing lung squamous cell carcinoma, which detects lung squamous cell carcinoma by detecting desmoglein 3 contained in a sample. The kit for diagnosing lung squamous cell carcinoma comprises the following reagents used in sandwich immunoassay:

(1) a DF366m antibody as an immobilized antibody; and
(2) an antibody selected from the group consisting of a DF151 antibody and an MAB1720 antibody (R&D Systems, Inc.).

The kit for diagnosing lung squamous cell carcinoma may further contain a substance, an instrument and the like that can be used for immobilization, detection and the like of the antibodies. For immobilization of the antibodies, a carrier such as a microtiter plate or an SPFS sensor chip, an immobilization liquid such as a carbonate buffer, and a blocking solution containing gelatin, albumin or the like can be incorporated into the kit. In addition, for detection of the antibodies, the kit may also contain, for example, a labeling substance, a labeled secondary antibody, and a substrate, carrier, washing buffer, sample diluent, enzyme substrate and stop solution that are required for label detection, as well as desmoglein 3 protein used as a purified standard substance, an instruction manual and the like. The content of the instruction manual usually includes the method of detecting lung squamous cell carcinoma according to the present invention and the method of detecting desmoglein 3 in a blood sample by sandwich immunoassay.

The kit for diagnosing lung squamous cell carcinoma can be constituted in accordance with the sandwich immunoassay to be employed. Further, in order to incorporate an assessment based on the expression level of an existing lung cancer marker(s) other than desmoglein 3 such as at least one selected from the group consisting of SCC and CYFRA, the kit may also contain a reagent(s) for detecting other lung cancer marker by sandwich immunoassay (e.g., an immobilized antibody and a detection antibody for other lung cancer marker) and the like.

<Application>

Among the above-described sandwich immunoassay methods, the ELISA method and the SPFS method are widely used for the measurement of blood samples.

ELISA is characterized in that it can use inexpensive reagents, does not require an expensive machine for measurement and particularly, is capable of processing a large number of samples simultaneously particularly by using a multi-well plate. Therefore, ELISA can be preferably used for, for example, primary screening of samples, such as processing of multiple samples for medical examination and the like.

Meanwhile, SPFS is inferior to plate ELISA in terms of the number of samples that it can process and has a drawback of requiring a special expensive machine. However, SPFS has an extremely high detection sensitivity and is thus capable of performing more detailed analyses. Therefore, SPFS can be preferably used in, for example, an application that requires high accuracy, such as definitive diagnosis of a sample assessed as false-positive in primary screening or basic research. Accordingly, in SPFS, detection of a target substance alone is not sufficient and it is usually required to set the detection cut-off value to be largely smaller than that of, for example, an ELISA method.

EXAMPLES

The present invention will now be described in detail by way of examples thereof; however, the present invention is not restricted thereto.

Example 1

<Test for Selecting Appropriate Antibodies Using Standard Antigens>

The following antibodies were used. The antibodies of (1) to (3) were all prepared from a culture supernatant of expression cells into which a hybridoma or a plasmid was introduced, which culture supernatant was produced by the method described in Patent Document 3.

(1) DF366m (DF366m[I] antibody)
(2) DF151 (DF151[I] antibody)
(3) D219-3 (Medical & Biological Laboratories Co., Ltd.)
(4) MAB1720 (R&D Systems, Inc., Catalog No.: MAB1720)

<Preparation of Biotin-labeled Antibodies>

Biotinylation of a monoclonal antibody was performed as follows.

To 1 mL of an antibody solution diluted with 50 mM sodium hydrogen carbonate solution (pH 8.5) to a concentration of 1 mg/mL, 10 μL of a solution prepared by dissolving Biotin-AC5-Osu (Dojindo Laboratories, Co., Ltd.) into a dimethylformamide at a concentration of 1.82 mg/mL was added, and the resultant was inversion-mixed at 25° C. for 2 hours. Then, this reaction solution was applied to a NAP-5 column (GE Healthcare, Inc.) to remove unreacted Biotin-AC5-Osu, and the solvent was replaced with calcium/magnesium-free phosphate-buffered saline (hereinafter, referred to as "PBS(−)") to obtain a biotinylated monoclonal antibody. The thus obtained biotinylated monoclonal antibody was diluted with PBS(−) to a concentration of 1 μg/mL and used as a biotinylated antibody solution.

<Preparation of Antigen Solutions>

A soluble-type human DSG3-mouse IgG2aFc fusion protein was prepared by binding the human DSG3 extracellular domain shown in SEQ ID NO:1 (Met1-Leu616) with the mouse IgG2 constant region and used as human desmoglein 3. This preparation of the fusion protein was carried out in the same manner as the method described in Example 3 of Patent Document 3. The thus obtained antigen protein was diluted with PBS(−) to prepare antigen solutions having a concentration of 0 to 25 ng/mL.

<ELISA Measurement>

Each solid-phase antibody was diluted with 100 mM sodium hydrogen carbonate buffer (pH 9.6) to a concentration of 5 μg/mL, and the resulting solution was added to a polystyrene ELISA plate (MaxiSorp Plate (trade name), manufactured by NUNC) in an amount of 50 μL/well. The ELISA plate was then incubated at 4° C. for 12 hours to immobilize the antibody.

Next, as a blocking solution, PBS(−) containing bovine serum albumin (hereinafter, referred to as "BSA") in an amount of 1% (hereinafter, this solution is referred to as "1% BSA-PBS(−)") was prepared and, after removing the antibody solution from the above plate, the thus prepared blocking solution was added in an amount of 100 μL/well. The plate was then incubated at 37° C. for 1 hour to perform blocking.

Subsequently, the antigen solutions having the above-described concentrations were each added to the plate in an amount of 50 μL/well, and the plate was incubated at room temperature for 1 hour. Then, the antigen solution was removed, and the plate was washed with 0.05% Tween 20-PBS three times. Thereafter, the 1-μg/mL biotinylated antibody solution was added in an amount of 50 μL/well, and the plate was incubated at room temperature for 1 hour.

After removing the biotinylated antibody solution and washing the plate with 0.05% Tween 20-PBS three times, streptavidin-bound horseradish peroxidase (Thermo Fisher Scientific Inc.; hereinafter, referred to as "streptavidin-HRP") prepared at a concentration of 12.5 ng/mL was added in an amount of 50 μL/well, and the plate was incubated at room temperature for 30 minutes.

Then, after removing the streptavidin-HRP solution and washing the plate with 0.05% Tween 20-PBS three times, a substrate solution (SuperSignal ELISA Femto Maximum Sensitivity Substrate (registered trademark); Pierce Biotechnology, Inc.) was added in an amount of 100 μL/well. One minute thereafter, the luminescence intensity was measured using a luminometer, Fluoroskan Ascent FL (trade name, Thermo Electron Corporation).

<Results>

The results are shown in Table 1. The numerical values shown in Table 1 represent the minimum values of the antigen solution concentration having an S/N ratio of higher than 2 (hereinafter, referred to as "detection limit concentration") and the unit of the numerical values is pg/mL. The S/N ratio was determined by dividing the luminescence intensity at the respective antigen solution concentrations (1.6, 8, 40, 200, 1,000, 5,000, and 25,000 pg/mL) by the luminescence intensity of an antigen-free blank antigen solution (0 pg/mL).

According to Table 1, a particularly high S/N ratio was obtained when DF366m was used as an immobilized antibody and DF151 was used as a detection antibody; therefore, it was revealed that the combination of these antibodies is the most preferred antibody combination to be used.

Further, Table 2 shows the S/N ratios at the respective sample concentrations for antibody combinations having a detection limit concentration of 1,000 pg/mL or less. Among those combinations having a detection limit concentration of 1,000 pg/mL or less, the S/N ratio was higher in the order of the combinations of DF151 (solid phase) and MAB1720 (detection), DF366m (solid phase) and MAB1720 (detection), MAB1720 (solid phase) and DF151 (detection), and DF151 (solid phase) and D219-3 (detection); therefore, it was revealed that these combinations are preferred in the order mentioned (Table 2). It is noted here that the underlined numerical values in Table 2 indicate the S/N ratios at the respective detection limit concentrations.

TABLE 1

| | | Detection antibody (biotinylated antibody) | | | |
|---|---|---|---|---|---|
| | | DF366m | DF151 | MAB1720 | D219-3 |
| Immobilized antibody | DF366m | 5,000 | 200 | 1,000 | 5,000 |
| | DF151 | 5,000 | 1,000 | 1,000 | 1,000 |
| | MAB1720 | 5,000 | 1,000 | 5,000 | 5,000 |
| | D219-3 | 5,000 | 5,000 | 5,000 | 5,000 |

TABLE 2

| | | Immobilized antibody | | | | | |
|---|---|---|---|---|---|---|---|
| | | DF151 | DF366m | DF151 | MAB1720 | DF366m | DF151 |
| | | Detection antibody | | | | | |
| | | D219-3 | | DF151 | | MAB1720 | |
| Desmoglein 3 concentration | 25000 | 50.3 | 186.0 | 55.2 | 53.0 | 80.4 | 82.2 |
| | 5000 | 9.2 | 37.3 | 11.1 | 11.4 | 16.6 | 17.7 |
| | 1000 | 2.3 | 8.1 | 2.8 | 2.8 | 3.9 | 4.1 |
| | 200 | 1.0 | 2.3 | 1.2 | 1.3 | 1.8 | 1.6 |
| | 40 | 0.8 | 1.2 | 0.9 | 1.0 | 0.9 | 1.1 |
| | 10 | 0.9 | 1.1 | 0.9 | 1.1 | 1.0 | 1.1 |
| | 1 | 0.8 | 1.0 | 0.9 | 0.9 | 0.9 | 1.0 |

Example 2

<Detection of Blood-Added Desmoglein 3 Standard>

Of the antibody combinations shown in Table 2, for those combinations having a detection limit concentration of 1,000 pg/mL or less, a sample in which a desmoglein 3 standard was added to human serum was measured.

The test was carried out in the same manner as in Example 1, except that the antigen solutions having a concentration of 0 to 25 ng/mL were prepared by diluting human desmoglein 3 with human serum (Kohjin Bio Co., Ltd., Catalog No.: 12181201). The test was not carried out for the combination of DF151 (solid phase) and D219-3 (detection) which had the lowest S/N ratio and the combination of the same antibodies, DF151 (solid phase) and DF151 (detection).

<Results>

The results are shown in Table 3. The numerical values shown in Table 3 represent the values of the detection limit concentration and the unit thereof is pg/mL. It was revealed that even the amount of desmoglein 3 contained in blood can be measured with high sensitivity by using the antibody combination of the present invention.

It was revealed that a particularly low detection limit concentration was attained when DF366m was used as an immobilized antibody and DF151 or MAB1720 was used as a detection antibody; and that, therefore, these combinations of antibodies are the preferred combinations to be used.

TABLE 3

| | | Detection antibody (biotinylated antibody) | | |
|---|---|---|---|---|
| | | DF366m | DF151 | MAB1720 |
| Immobilized antibody | DF366m | | 200 | 200 |
| | DF151 | | | 1,000 |
| | MAB1720 | | 1,000 | |

Example 3

<Detection of Desmoglein 3 in Blood (Serum and Plasm) Samples of Patients by Sandwich ELISA>

Detection of desmoglein 3 in blood samples of cancer patients was performed as follows.

<Preparation of Test Solutions>

Human blood samples obtained from a blood bank (serum or plasma) (10 samples each for healthy individuals, pancreatic cancer patients, lung adenocarcinoma patients and lung squamous cell carcinoma patients) were 10-fold diluted with bovine pooled serum (Kohjin Bio Co., Ltd.) to prepare test solutions.

<ELISA Measurement>

DF366m was diluted with 100 mM sodium hydrogen carbonate buffer (pH 9.6) to a concentration of 5 µg/mL, and the resulting solution was added to a polystyrene ELISA plate (MaxiSorp Plate (trade name), manufactured by NUNC) in an amount of 50 µL/well. The ELISA plate was then incubated overnight at 4° C. to immobilize the antibody.

After removing the antibody solution, 1% BSA-PBS(−) (blocking solution) was added in an amount of 100 µL/well, and the plate was incubated at room temperature for 2 hours to perform blocking.

Subsequently, after removing the blocking solution and washing the plate with 0.05% Tween 20-PBS three times, the test solution was added in an amount of 50 µL/well, and the plate was incubated at room temperature for 1 hour. Then, the test solution was removed, and the plate was washed with 0.05% Tween 20-PBS three times. Thereafter, a 1-µg/mL biotinylated DF-151 antibody solution (1% BSA-PBS(−)) was added in an amount of 50 µL/well, and the plate was incubated at room temperature for 1 hour.

After removing the biotinylated DF-151 antibody solution and washing the plate with 0.05% Tween 20-PBS three times, a streptavidin-HRP solution (Thermo Fisher Scientific Inc.) prepared at a concentration of 12.5 ng/mL was added in an amount of 50 µL/well, and the plate was incubated at room temperature for 30 minutes.

Then, after removing the streptavidin-HRP solution and washing the plate with 0.05% Tween 20-PBS three times, a substrate solution (SuperSignal ELISA Femto Maximum Sensitivity Substrate (registered trademark); Pierce Biotechnology, Inc.) was added in an amount of 100 µL/well. One minute thereafter, the luminescence intensity was measured using a luminometer, Fluoroskan Ascent FL (trade name, Thermo Electron Corporation).

<Measurement Results>

The results are shown in FIG. 1. In one sample of a lung squamous cell carcinoma patient, the presence of desmoglein 3 was detected with a significantly higher concentration as compared to the healthy individuals. In the samples of the healthy individuals, pancreatic cancer patients and lung adenocarcinoma patients, no large increase in the desmoglein 3 concentration was found. Therefore, it was able to distinguish lung squamous cell carcinoma from other cancers, and it was suggested that the blood desmoglein 3 level can be used as a specific diagnostic marker for lung squamous cell carcinoma.

Example 4

<Detection of Desmoglein 3 in Blood (Serum) Samples of Lung Squamous Cell Carcinoma Patients>

Blood samples of 30 lung squamous cell carcinoma patients were obtained from a blood bank and subjected to an additional experiment. The additional experiment was carried out in the same manner as in Example 2, except that undiluted solutions were used as test solutions. The results thereof were evaluated along with the measurement results obtained in Example 2 for 10 healthy individuals and 10 lung squamous cell carcinoma patients.

The results are shown in FIG. 2. The numbers placed below each bar graph indicate the sample numbers. The blood desmoglein 3 concentration was found to be about 0 to 4 ng/mL for the 10 healthy individuals. Taking into consideration that the detection limit of the blood desmoglein 3 in the measurement using ELISA is 200 pg/mL, the cut-off value for the assessment of lung squamous cell carcinoma was set at 1 ng/mL. In this case, a desmoglein 3 was detected at a concentration of not lower than the cut-off value in the blood samples of 20 out of the 40 lung squamous cell carcinoma patients (positive ratio=50%).

A desmoglein 3 concentration of not lower than the cut-off value was detected in the blood samples of 3 out of 10 healthy individuals (false-positive ratio=30%). Therefore, it was demonstrated that the blood desmoglein 3 level can be used as a diagnostic marker for lung squamous cell carcinoma.

Moreover, similar results were obtained when DF366m was used as an immobilized antibody and biotinylated MAB1720 was used as a detection antibody; however, when other antibody combinations such as a combination of MAB1720 (solid phase) and DF151 (detection) was used, a required detection sensitivity was not attained and the difference between the healthy individuals and the patients was thus not clear.

From the above, it was shown that, in the ELISA method as well, by using the antibody combination of the present invention, the human blood desmoglein 3 level can be detected with a sensitivity required for detection of lung squamous cell carcinoma.

Furthermore, similar values were obtained when the desmoglein 3 concentration was measured in a serum sample and a plasma sample that were collected from the same patient; therefore, it was confirmed that the desmoglein 3 concentration in plasma can also be measured in the same manner.

Example 5

<Comparison with Other Lung Cancer Markers>

For the blood samples collected from the 40 lung squamous cell carcinoma patients of Example 3, desmoglein 3 was compared with other lung cancer markers in terms of their properties. As the data of desmoglein 3, the results of Example 3 were used. As other lung cancer markers, SCC and CYFRA21-1 (hereinafter, referred to as "CYFRA") were selected and examined.

<Measurement of SCC and CYFRA>

Measurement of SCC was performed using an SCC measurement kit, CanAg SCC EIA (trade name, FUJIREBIO Diagnostics, Inc.), in accordance with the attached instructions, and the cut-off value was set at 1.5 ng/mL. Measurement of CYFRA was performed using a CYFRA measurement kit, CYFRA21-1 EIA (trade name, FUJIREBIO Diagnostics, Inc.), in accordance with the attached instructions, and the cut-off value was set at 3.5 ng/mL.

It is noted here that the reference values of these markers are generally recognized as 1.5 ng/mL and 2.0 ng/mL, respectively (The Medical Frontline, Extra Edition, "Lung Cancer" (Saishin Igaku-sha), 2012).

<Results>

The results are shown in FIGS. 3 to 5. Naturally, a negative value cannot normally be expected for blood concentration; however, in a concentration range near the quantitation limit, a noise value often exceeds a signal value. Thus, negative values were calculated and, in FIGS. 3 to 5, they are shown as calculated.

From FIGS. 3 and 4, since desmoglein 3, SCC and CYFRA showed different expression trends, there was found no correlation between desmoglein 3 and SCC or CYFRA in terms of their expression. SCC and CYFRA showed similar expression trends (FIG. 5). That is, by measuring and assessing the presence of desmoglein 3 in blood, it was able to diagnose the lung squamous cell carcinoma patients with lung squamous cell carcinoma, which patients could not have been assessed to have cancer by using the existing lung cancer markers.

Furthermore, it was shown that the detection performance for lung squamous cell carcinoma is improved by using the measurement results for the blood levels of desmoglein 3, SCC and CYFRA in combination. That is, when desmoglein 3 (with the cut-off value being set at 1 ng/mL), SCC and CYFRA were used individually, the detection rate was 20/40, 4/40 and 6/40, respectively, while the detection rate was 21/40 when desmoglein 3 and SCC were used in combination, 20/40 when desmoglein 3 and CYFRA were used in combination, and 21/40 when these three markers were all used in combination. In this case, the false-positive ratio of desmoglein 3 was 3/10 (30%).

When desmoglein 3 whose cut-off value was set at 2 ng/mL, SCC and CYFRA were used individually, the detection rate was 13/40, 4/40 and 6/40, respectively, while the detection rate was 15/40 when desmoglein 3 and SCC were used in combination, 15/40 when desmoglein 3 and CYFRA were used in combination, and 17/40 when these three markers were all used in combination. In this case, the false-positive ratio of desmoglein 3 was 1/10 (10%). Thus, by using desmoglein 3 in combination with SCC and/or CYFRA, it was possible to maintain high detection performance while reducing the false-positive ratio of desmoglein 3.

Here, those samples that showed a high desmoglein 3 value when measured with the antibody combination used in Example 3 (DF366m+biotinylated DF-151) also showed a high desmoglein 3 value when measured with other antibody combinations used in Example 1. Conversely, those samples that showed a low desmoglein 3 value in the former case also showed a low desmoglein 3 value in the latter case in the same manner. That is, also when the measurement was performed with an antibody combination other than the combination of DF366m and biotinylated DF-151, it was able to diagnose the lung squamous cell carcinoma patients with lung squamous cell carcinoma, which patients could not have been assessed to have cancer by the existing lung cancer markers.

Example 6

<Detection of Desmoglein 3 Standard in Buffer by SPFS (1)>

Desmoglein 3 in a buffer was measured by SPFS. DF366m and DF151 that are described in Example 1 were used as an immobilized antibody and a detection antibody, respectively.

(1) Preparation of Sensor Chip

A 1 mm-thick glass transparent support "S-LAL 10" (Ohara Inc., refractive index (nd): 1.72) was washed with plasma. Then, on one side of the support, a chromium thin film was formed by sputtering, and a gold thin film was further formed on the surface of the chromium thin film by sputtering. The chromium thin film had a thickness of 1 to 3 nm or less, and the gold thin film had a thickness of 42 to 47 nm.

The thus obtained transparent support having the metal thin films was immersed for 24 hours in 10 mL of an ethanol solution of 11-amino-1-undecanethiol adjusted to have a concentration of 1 mM, thereby forming an SAM on the surface of the gold thin film. The resulting transparent support was taken out of the ethanol solution, washed with each of ethanol and isopropanol, and then dried using an air-blow gun.

Subsequently, the thus obtained SAM-equipped transparent support was immersed for 1 hour in a pH 7.4 MES-buffered saline (MES) (ionic strength: 10 mM) containing 1 mg/mL of carboxymethyldextran (CMD) having a molecular weight of 500,000 to 1,000,000, 0.5 mM of N-hydroxysuccinimide (NHS) and 1 mM of 1-ethyl-3-(3-dimethylaminopropyl)carbodiimide hydrochloride (EDC) as water-soluble carbodiimide (WSC), thereby fixing CMD on the SAM surface as an immobilization layer. Then, the resulting transparent support was immersed in 1M aqueous NaOH solution for 30 minutes to hydrolyze unreacted succinate. The immobilization layer made of CMD had an average thickness of 70 nm and a density of 1.9 ng/mm$^2$.

Subsequently, after immersing the thus obtained immobilization layer-equipped transparent support in an MES containing 50 mM of NHS and 100 mM of WSC for 1 hour, the transparent support was further immersed in a DF366m antibody solution (2.5 μg/mL) for 30 minutes, thereby immobilizing the monoclonal antibody with CMD.

Further, by circulating PBS containing 1% by mass of bovine serum albumin (BSA) and 1 M of aminoethanol for 30 minutes, a treatment for inhibition of non-specific adsorption was performed.

On the sensor chip obtained in the above-described manner, a 0.5 mm-thick PDMS sheet having a hole of 10 mm in length and 5 mm in width was mounted, and a silicone rubber spacer was arranged around the PDMS sheet. On top of these PDMS sheet and silicone rubber spacer, a PMMA top plate, on which a hole for liquid introduction and a hole for liquid discharge were formed at the position corresponding to the hole of the PDMS sheet, was mounted. Then, the resulting laminate composed of the sensor chip, the PDMS sheet, the silicone rubber spacer and the PMMA top plate was pressed at the periphery and screw-fixed to prepare a SPFS measurement member.

(2) Preparation of Fluorescently Labeled Ligand

Using a DF151 antibody solution (2.5 μg/mL) and Alexa Fluor 647 labeling kit (Invitrogen), an Alexa Fluor 647-labeled DF151 antibody was prepared in accordance with the prescribed procedures of the kit. Then, unreacted matters were removed using a molecular weight cut filter (Nihon Millipore K.K.), and the Alexa Fluor 647-labeled DF151 antibody was purified and stored at 4° C. until the following assay.

(3) Execution of Assay

To the flow path of the measurement member prepared in the above-described step (1), 0.1 mL of a PBS solution containing 100 pg/mL (=0.1 ng/mL) of desmoglein 3 was fed and circulated in the flow path for 25 minutes.

Subsequently, a Tris-buffered saline (TBS) containing 0.05% by mass of Tween 20 was fed and circulated in the flow path for 10 minutes to wash the flow path. Then, a PBS solution containing 2 μg/mL of the Alexa Fluor 647-labeled DF151 prepared in the above-described step (2) was fed and circulated for 5 minutes.

Once again, a Tris-buffered saline (TBS) containing 0.05% by mass of Tween 20 was fed and circulated in the flow path for 10 minutes to wash the flow path. Then, with the flow path being filled with PBS buffer (pH 7.4), the assay area was irradiated with laser light (640 nm, 40 μW) from the back side of the metal thin films, and the fluorescence intensity was measured using a photomultiplier tube (PMT)

arranged above the assay area. The thus measured value was defined as "signal" (S) at a desmoglein 3 concentration of 100 pg/mL.

On another front, the fluorescence intensity was also measured by the same procedures as described above, except that a PBS solution containing no desmoglein 3 (0 pg/mL) was fed in place of the PBS solution containing 100 pg/mL of desmoglein 3. The thus measured value was defined as "noise" (N).

Further, the fluorescence intensity was measured by the same procedures as described above, except that the desmoglein 3 concentration of the fed PBS solution was changed to 10,000 pg/mL, 5,000 pg/mL, 1,000 pg/mL, 200 pg/mL, 50 pg/mL, 10 pg/mL, 3.16 pg/mL, 1 pg/mL, 0.316 pg/mL, 0.1 pg/mL and 0.031 pg/mL. The thus measured values were each defined as "signal" (S) at the respective concentrations.

<Results>

The results are shown in FIG. 6. The ordinate represents the value of "signal"-"noise" (S-N) (unit: a.u.) and the abscissa represents the desmoglein 3 concentration (unit: pg/mL). Based on this plot, it can be determined that the detection limit concentration of desmoglein 3 by the above-described measurement system is 5 pg/mL, and it was revealed that this measurement system can attain a detection sensitivity that is about 40 times higher than that of the measurement by sandwich ELISA. That is, the SPFS method attains an effect that an equivalent evaluation can be performed with a sample amount that is 1/40 of the sample amount required for the ELISA method.

In addition, when the antibody combination was variously changed in the same manner as in Example 1, it was confirmed that plots similar to the one shown in FIG. 6 can be obtained. Moreover, by comparing the S/N ratios in the concentration range of 200 to 1,000 pg/mL, it was found that the S/N ratio was higher when DF366m was used as an immobilized antibody and DF151 was used as a detection antibody, followed by other antibody combinations in the order of DF366 (solid phase) and MAB1720 (detection), DF151 (solid phase) and MAB1720 (detection), MAB1720 (solid phase) and DF151 (detection), and DF151 (solid phase) and D219-3 (detection), and this order was almost the same as the one obtained in Example 1. That is, the S/N ratios at a concentration of 1,000 pg/mL were, in the order described above, 140.0, 92.2, 60.8, 34.5 and 24.4.

A particularly high S/N ratio was obtained when DF366m was used as an immobilized antibody and DF151 was used as a detection antibody as well as when a combination of DF366 (solid phase) and MAB1720 (detection) was used; therefore, it was revealed that these are the most preferred antibody combinations.

Example 7

<Detection of Blood-Added Desmoglein 3 Standard by SPFS>

Detection was performed in the same manner as in Example 6, except that the antibody solution prepared in Example 2 was used as a sample.

<Results>

Results similar to those of Example 6 were obtained, and the detection limit concentration of desmoglein 3 in blood was determined to be 5 pg/mL. That is, it was revealed that, with the use of the sample combination of the present invention, desmoglein 3 in blood samples can be detected with superior sensitivity by SPFS. It was also shown that SPFS can detect desmoglein 3 with a far smaller sample amount as compared to other measurement methods such as an ELISA method and that, in SPFS, the cut-off value for the determination of lung squamous cell carcinoma can be further reduced than in an ELISA method.

From the above, it was shown that, in the SPFS method, by using the antibody combination of the present invention, the human blood desmoglein 3 level can be detected with a sensitivity required for highly accurate detection of lung squamous cell carcinoma.

The list of the amino acid sequences of the human desmoglein 3 protein and its monoclonal antibodies that are used in the present invention is provided below.

TABLE 4

| SEQ ID NO: | Notation | Sequence |
|---|---|---|
| 1 | hDSG3 | MMGLFPRTTGALAIFVVVILVHGELRIETKGQYDEEEMTMQQAKRRQK REWVKFAKPCREGEDNSKRNPIAKITSDYQATQKITYRISGVGIDQPPFG IFVVDKNTGDINITAIVDREETPSFLITCRALNAQGLDVEKPLILTVKILDIN DNPPVFSQQIFMGEIEENSASNSLVMILNATDADEPNHLNSKIAFKIVSQ EPAGTPMFLLSRNTGEVRTLTNSLDREQASSYRLVVSGADKDGEGLST QCECNIKVKDVNDNFPMFRDSQYSARIEENILSSELLRFQVTDLDEEYT DNWLAVYFFTSGNEGNWFEIQTDPRTNEGILKVVKALDYEQLQSVKLSI AVKNKAEFHQSVISRYRVQSTPVTIQVINVREGIAFRPASKTFTVQKGISS KKLVDYILGTYQAIDEDTNKAASNVKYVMGRNDGGYLMIDSKTAEIKFV KNMNRDSTFIVNKTITAEVLAIDEYTGKTSTGTVYVRVPDFNDNCPTAVL EKDAVCSSSPSVVVSARTLNNRYTGPYTFALEDQPVKLPAVWSITTLNAT SALLRAQEQIPPGVYHISLVLTDSQNNRCEMPRSLTLEVCQCDNRGICG TSYPTTSPGTRYGRPHSGRLGPAAIGULLGULLLLAPLULTCDCGAGS TGGVTGGFIPVPDGSEGTIHQWGIEGAHPEDKEITNICVPPVTANGADF MESSEVCTNTYARGTAVEGTSGMEMTTKLGAATESGGAAGFATGTVS GAASGFGAATGVGICSSGQSGTMRTRHSTGGTNKDYADGAISMNFLDS YFSQKAFACAEEDDGQEANDCLLIYDNEGADATGSPVGSVGCCSFIAD DLDDSFLDSLGPKFKKLAEISLGVDGEGKEVQPPSKDSGYGIESCGHPI EVQQTGFVKCQTLSGSQGASALSASGSVQPAVSIPDPLQHGNYLVTETY SASGSLVQPSTAGFDPLLTQNVIVTERVICPISSVPGNLAGPTQLRGSHT MLCTEDPCSRLI |
| 2 | DF366m_H_IgG2a | EVQLQQSGPELVKPGASVKISCKASGYTFTDYNMDWVKQSHGESLEWI GYIYPNNGGSGYNQKFKSKATLTVDKSSSTAYMELHSLTSEDSAVYYCA RRDSYYGFDMAWFAYWGQGTLVTVSAAKTTAPSVYPLAPVCGDTTGSS VTLGCLVKGYFPEPVTLTWNSGSLSSGVHTFPAVLQSDLYTLSSSVTVTS STWPSQSITCNVAHPASSTKVDKKIEPRGPIIKPCPPCKCPAPNLLGGPS |

TABLE 4-continued

| SEQ ID NO: | Notation | Sequence |
|---|---|---|
| | | VFIFPPKIKDVLMISLSPIVTCVVVDVSEDDPDVQISWFVNNVEVHTAQT QTHREDYNSTLRVVSALPIQHQDWMSGKEFKCKVNNKDLPAPIERTISK PKGSVRAPQVYVLPPPEEEMTKKQVTLTCMVTDFMPEDIYVEWTNNGK TELNYKNTEPVLDSDGSYFMYSKLRVEKKNWVERNSYSCSVVHEGLHN HHTTKSFSRTPGK |
| 3 | DF366m_L_kappa | DIQMTQSPASLSASVGETVTITCRPSENIYNNLAWYQQKQGKSPQLLVY VATNLAEGVPSRFSGSGSGTRFSLKINSLQPEDFGKYYCQHSYGTPWTF GGGTKLEIKRADAAPTVSIFPPSSEQLTSGGASVVCFLNNFYPKDINVKW KIDGSERQNGVLNSWTDQDSKDSTYSMSSTLTLTKDEYERHNSYTCEA THKTSTSPIVKSFNRNEC |
| 4 | DF366m_HCDR1 | DYNMD |
| 5 | DF366m_HCDR2 | YIYPNNGGSGYNQKFKS |
| 6 | DF366m_HCDR3 | RDSYYGFDMAWFAY |
| 7 | DF366m_LCDR1 | RPSENIYNNLA |
| 8 | DF366m_LCDR2 | VATNLAE |
| 9 | DF366m_LCDR3 | QHSYGTPWT |
| 10 | DF366m_VH | EVQLQQSGPELVKPGASVKISCKASGYTFTDYNMDWVKQSHGESLEWI GYIYPNNGGSGYNQKFKSKATLTVDKSSSTAYMELHSLTSEDSAVYYCA RRDSYYGFDMAWFAYWGQGTLVTVSA |
| 11 | DF366m_VL | DIQMTQSPASLSASVGETVTITCRPSENIYNNLAWYQQKQGKSPQLLVY VATNLAEGVPSRFSGSGSGTRFSLKINSLQPEDFGKYYCQHSYGTPWTF GGGTKLEIK |
| 12 | DF366m_CH1 | AKTTAPSVYPLAPVCGDTTGSSVTLGCLVKGYFPEPVTLTWNSGSLSSG VHTFPAVLQSDLYTLSSSVTVTSSTWPSQSITCNVAHPASSTKVDKKIEP RGMIK |
| 13 | CL_kappa | RADAAPTVSIFPPSSEQLTSGGASVVCFLNNFYPKDINVKWKIDGSERQ NGVLNSWTDQDSKDSTYSMSSTLTLTKDEYERHNSYTCEATHKTSTSPI VKSFNRNEC |
| 14 | DF366m_H_IgG1 | EVQLQQSGPELVKPGASVKISCKASGYTFTDYNMDWVKQSHGESLEWI GYIYPNNGGSGYNQKFKSKATLTVDKSSSTAYMELHSLTSEDSAVYYCA RRDSYYGFDMAWFAYWGQGTLVTVSAAKTTPPSVYPLAPGSAAQTNSM VTLGCLVKGYFPEPVTVTWNSGSLSSGVHTFPAVLQSDLYTLSSSVTVP SSTWPSQTVTCNVAHPASSTKVDKKIVPRDCGCKPCICTVPEVSSVFIFP PKPKDVLTITLTPKVTCVVVDISKDDPEVQFSWFVDDVEVHTAQTKPRE EQFNSTFRSVSELPIMHQDWLNGKEFKCRVNSAAFPAPIEKTISKTKGR PKAPQVYTIPPPKEQMAKDKVSLTCMITDFFPEDITVEWQWNGQPAENY KNTQPIMDTDGSYFVYSKLNVQKSNWEAGNTFTCSVLHEGLHNHHTEK SLSHSPGK |
| 15 | DF151_H_IgG2b | EVQLQQSGPELVKPGASVKISCKASGYSFTAYYMHWVKQSPEKCLEWI GQINPSTGGTTYNQKFKAKATLTVDKSSSTAYMQLKSLTSEDSAVYYCA RWGDSWGQGTTLTVSSAKTTPPSVYPLAPGCGDTTGSSVTLGCLVKGY FPESVTVTWNSGSLSSSVHTFPALLQSGLYTMSSSVTVPSSTWPSQTVT CSVAHPASSTTVDKKLEPSGPISTINPCPPPCKECHKCPAPNLEGGPSVFI FPPNIKDVLMISLTPKVTCVVVDVSEDDPDVQISWFVNNVEVHTAQTQT HREDYNSTIRVVSALPIQHQDWMSGKEFKCKVNNKDLPSPIERTISKIK GLVRAPQVYILPPPAEQLSRKDVSLTCLVVGFNPGDISVEWTSNGHTEE NYKDTAPVLDSDGSYFIYSKLDIKTSKWEKTDSFSCNVRHEGLKNYYLK KTISRSPGK |
| 16 | DF151_L_kappa | DIVLTQSPASLAVSLGQSVTISCRASESVEYYGTSLMQWYQQKPGQPPK LLIYGASDVESGVPARFSGSGSGTDFSLNIHPVEEDDIAMYFCQQSRKV PYTFGSGTKLEIKRADAAPTVSIFPPSSEQLTSGGASVVCFLNNFYPKDIN VKWKIDGSERQNGVLNSWTDQDSKDSTYSMSSTLTLTKDEYERHNSYT CEATHKTSTSPIVKSFNRNEC |

TABLE 4-continued

| SEQ ID NO: | Notation | Sequence |
|---|---|---|
| 17 | DF151_HCDR1 | AYYMH |
| 18 | DF151_HCDR2 | QINPSTGGTTYNQKFKA |
| 19 | DF151_HCDR3 | WGDS |
| 20 | DF151_LCDR1 | RASESVEYYGTSLMQ |
| 21 | DF151_LCDR2 | GASDVES |
| 22 | DF151_LCDR3 | QQSRKVPYT |
| 23 | DF151_VH | EVQLQQSGPELVKPGASVKISCKASGYSFTAYYMHWVKQSPEKCLEWIGQINPSTGGTTYNQKFKAKATLTVDKSSSTAYMQLKSLTSEDSAVYYCARWGDSWGQGTTLTVSS |
| 24 | DF151_VL | DIVLTQSPASLAVSLGQSVTISCRASESVEYYGTSLMQWYQQKPGQPPKLLIYGASDVESGVPARFSGSGSGTDFSLNIHPVEEDDIAMYFCQQSRKVPYTFGSGTKLEIK |
| 25 | DF151_CH1 | AKTTPPSVYPLAPGCGDTTGSSVTLGCLVKGYFPESVTVTWNSGSLSSSVHTFPALLQSGLYTMSSSVTVPSSTWPSQTVTCSVAHPASSTTVDKKLEPSGPISTINPCP |

Sequence Listing Free Text

SEQ ID NO:2: artificial sequence DF366 VH—Murine IgG2a CH (H chain variable region of DF366—H chain constant region of mouse IgG2a)

SEQ ID NO:3: artificial sequence DF366 VL—Murine IgG2a CL (kappa) (L chain variable region of DF366—L chain (κ chain) constant region of mouse IgG2a)

The invention claimed is:

1. A method of detecting desmoglein 3 content in a blood sample from a subject, the method comprising the steps of:
    (1) measuring desmoglein 3 content in the blood sample collected from the subject; and
    (2) comparing the desmoglein 3 content measured in step (1) with the desmoglein 3 content in a blood sample collected from a healthy individual; and
    (3) setting a cut-off value for desmoglein 3 content such that a false positive ratio is 30% or less,
    wherein said measuring in step (1) is performed by a sandwich immunoassay, and
    wherein said sandwich immunoassay uses:
        as an immobilized antibody, a DF366m antibody being a complete antibody comprising an H chain represented by the amino acid sequence shown in SEQ ID NO: 2 and an L chain represented by SEQ ID NO: 3, or an antibody comprising an H chain having the amino acid sequence shown in SEQ ID NO: 10 as VH and an L chain having the amino acid sequence shown in SEQ ID NO: 11 as VL;
        said DF366m antibody having HCDR1 represented by the amino acid sequence shown in SEQ ID NO:4, HCDR2 represented by the amino acid sequence shown in SEQ ID NO:5, HCDR3 represented by the amino acid sequence shown in SEQ ID NO:6, LCDR1 represented by the amino acid sequence shown in SEQ ID NO:7, LCDR2 represented by the amino acid sequence shown in SEQ ID NO:8 and LCDR3 represented by the amino acid sequence shown in SEQ ID NO:9; and,
        as a detection antibody an MAB1720 antibody or a DF151 antibody being a complete antibody comprising an H chain represented by the amino acid sequence shown in SEQ ID NO:15 and an L chain represented by SEQ ID NO:16, or an antibody comprising an H chain having the amino acid sequence shown in SEQ ID NO:23 as VH and an L chain having the amino acid sequence shown in SEQ ID NO:24 as VL;
        said DF151 antibody having HCDR1 represented by the amino acid sequence shown in SEQ ID NO:17, HCDR2 represented by the amino acid sequence shown in SEQ ID NO:18, HCDR3 represented by the amino acid sequence shown in SEQ ID NO:19, LCDR1 represented by the amino acid sequence shown in SEQ ID NO:20, LCDR2 represented by the amino acid sequence shown in SEQ ID NO:21 and LCDR3 represented by the amino acid sequence shown in SEQ ID NO:22,
    wherein said sandwich immunoassay is surface plasmon-field enhanced fluorescence spectroscopy and has a signal to noise ratio of 60.8 to 140 at a desmoglein 3 concentration of 1,000 pg/ml.

2. The method according to claim 1, further incorporating an assessment based on the expression level of at least one lung cancer marker selected from the group consisting of SCC and CYFRA.

3. The method according to claim 1, wherein, in said sandwich immunoassay, said sample is brought into contact with said DF366m antibody immobilized on a carrier and then with said DF151 antibody or said MAB1720 antibody.

* * * * *